United States Patent
Silagy et al.

(12) 
(10) Patent No.: US 10,265,568 B2
(45) Date of Patent: Apr. 23, 2019

(54) PRONATOR SUPINATOR WRIST DEVIATOR EXERCISE DEVICE

(71) Applicant: COGNATUS INNOVATIONS LLC, Waban, MA (US)

(72) Inventors: Robert Silagy, Merrick, NY (US); Dennis Waldman, Waban, MA (US)

(73) Assignee: Cognatus Innovations LLC, Waban, MA (US)

( * ) Notice: Subject to any disclaimer, the term of this patent is extended or adjusted under 35 U.S.C. 154(b) by 371 days.

(21) Appl. No.: 15/130,049

(22) Filed: Apr. 15, 2016

(65) Prior Publication Data

US 2016/0303420 A1 Oct. 20, 2016

Related U.S. Application Data

(60) Provisional application No. 62/147,894, filed on Apr. 15, 2015.

(51) Int. Cl.
*A63B 21/00* (2006.01)
*A61B 5/11* (2006.01)
(Continued)

(52) U.S. Cl.
CPC ........ *A63B 21/4035* (2015.10); *A61B 5/1128* (2013.01); *A63B 21/072* (2013.01); *A63B 21/075* (2013.01); *A63B 23/14* (2013.01); *A63B 71/0622* (2013.01); *G09B 19/0038* (2013.01); *A63B 21/00072* (2013.01); *A63B 21/0602* (2013.01); *A63B 21/0608* (2013.01); *A63B 24/0087* (2013.01); *A63B 2022/0094* (2013.01); *A63B 2071/065* (2013.01); *A63B 2071/068* (2013.01); *A63B 2071/0625* (2013.01); *A63B 2207/00* (2013.01); *A63B 2207/02* (2013.01); *A63B 2208/0204* (2013.01); *A63B 2208/0233* (2013.01); *A63B 2220/16* (2013.01);
(Continued)

(58) Field of Classification Search
None
See application file for complete search history.

(56) References Cited

U.S. PATENT DOCUMENTS 1,333,005 A * 3/1920 Warner ............. A63B 21/0608
482/110
4,381,111 A * 4/1983 Richards ............. A63B 69/365
473/229

(Continued)

*Primary Examiner* — Joshua Lee
(74) *Attorney, Agent, or Firm* — Carter, DeLuca & Farrell LLP

(57) ABSTRACT

A pronation supination wrist deviator exercise device includes a handle having a proximal portion and a distal portion; a shaft defining a longitudinal axis extending from a proximal end to a distal end; and a head portion having a predetermined weight. The head portion or the handle are mounted for relative movement on the shaft between a first position and a second position. The head portion and the handle define a first distance. The predetermined weight of the head portion represents a first weight. The first weight multiplied by the first distance represents a first effective torque of the device. When the distance between the head portion and the distal portion of the handle is changed to at least a second distance, the first weight multiplied by the second distance represents at least a second effective torque of the device.

16 Claims, 17 Drawing Sheets

(51) Int. Cl.
    *A63B 23/14*    (2006.01)
    *A63B 71/06*    (2006.01)
    *G09B 19/00*    (2006.01)
    *A63B 21/072*   (2006.01)
    *A63B 21/075*   (2006.01)
    *A63B 21/06*    (2006.01)
    *A63B 22/00*    (2006.01)
    *A63B 24/00*    (2006.01)

(52) U.S. Cl.
    CPC ....... *A63B 2220/17* (2013.01); *A63B 2220/44* (2013.01); *A63B 2220/54* (2013.01); *A63B 2225/09* (2013.01); *A63B 2225/20* (2013.01); *A63B 2225/50* (2013.01)

(56) References Cited

U.S. PATENT DOCUMENTS

| | | | | |
|---|---|---|---|---|
| 4,934,706 A * | 6/1990 | Marshall | ............ | A63B 69/3632 33/334 |
| 4,993,710 A * | 2/1991 | Marshall | ............ | A63B 69/3632 33/334 |
| 5,209,481 A * | 5/1993 | DeBack | ............ | A63B 21/0004 473/220 |
| 5,281,192 A * | 1/1994 | Nelson | ............ | A63B 15/00 482/105 |
| 6,152,858 A * | 11/2000 | Kolb | ............ | A63B 23/14 482/100 |
| 6,398,663 B1 * | 6/2002 | Lin | ............ | A63B 69/3632 473/220 |
| 7,942,785 B1 * | 5/2011 | Russell | ............ | A61B 5/1121 482/44 |
| D653,715 S * | 2/2012 | Tumminia | ............ | D21/662 |
| 8,858,406 B2 * | 10/2014 | Klukas | ............ | A63B 15/00 482/108 |
| 9,028,378 B2 * | 5/2015 | Shah | ............ | A63B 60/04 482/109 |
| 9,498,676 B1 * | 11/2016 | Emick | ............ | A63B 23/04 |
| 9,782,655 B1 * | 10/2017 | Novosel, Sr. | ............ | A63B 69/0002 |
| 10,029,142 B2 * | 7/2018 | Koenig | ............ | A63B 21/075 |
| 2004/0043824 A1 * | 3/2004 | Uzelac | ............ | A63B 69/0059 473/266 |
| 2004/0063553 A1 * | 4/2004 | Viscount | ............ | A63B 21/065 482/107 |
| 2004/0107592 A1 * | 6/2004 | Mattis | ............ | A61B 5/1071 33/512 |
| 2007/0135273 A1 * | 6/2007 | Ljevaja | ............ | A63B 15/00 482/108 |
| 2011/0230275 A1 * | 9/2011 | Hicks | ............ | A63B 53/007 473/220 |
| 2012/0088641 A1 * | 4/2012 | Shah | ............ | A61H 1/0274 482/110 |
| 2014/0024473 A1 * | 1/2014 | Reid | ............ | A63B 53/0487 473/313 |
| 2014/0315653 A1 * | 10/2014 | Wong | ............ | A63B 69/3685 473/241 |
| 2015/0174445 A1 * | 6/2015 | Robertson, Jr. | ............ | A63B 23/0405 482/93 |
| 2016/0038780 A1 * | 2/2016 | Hugou | ............ | A47C 3/029 482/8 |
| 2017/0225026 A1 * | 8/2017 | Shah | ............ | A63B 21/075 |

* cited by examiner

PRONATOR SUPINATOR WRIST DEVIATOR EXERCISE DEVICE

CROSS-REFERENCE TO RELATED APPLICATIONS

This application claims the benefit of, and priority to, U.S. Provisional Patent Application No. 62/147,894 by Robert Silagy et al. entitled "PRONATOR-SUPINATOR HAMMER", filed on Apr. 15, 2015, the entire contents of which is incorporated by reference herein.

BACKGROUND

Technical Field

The present disclosure relates generally to devices and apparatuses for therapeutic exercises and more particularly for devices and apparatuses for pronation and supination and wrist deviator exercises.

Description of Related Art

Pronation and supination are a pair of unique movements possible only in the forearms and hands, allowing the human body to flip the palm either face up or face down.

In both Physical and Occupational therapy, therapists have their patients perform exercises for injured rotator cuffs, tennis elbow, and golf elbow. Accordingly such exercises are called Pronation and Supination.

For Tennis Elbow and Golf Elbow injuries or strengthening, the exercises are performed sitting with the patient's forearm on their thigh. For Rotator Cuff injuries, the exercises are performed while standing with the patient's elbow straight and arm out in front of them.

Another exercise to improve wrist strength requires a hammering motion. These exercises involve rotating the forearm and hand +/−90 degrees while holding a weight at the end of a levered arm (rod). This exercise is called Wrist Deviator.

In all these exercises, it is desirable for the therapist to know how much "effective" weight at the end of the device the patient is using.

Another exercise to improve patient performance is called "Fatigue Training". Where the patient starts with certain "effective" weight until they are exhausted and then the "effective" weight is quickly decreased. The patient continues exercising until again exhausted. Then the "effective" weight is quickly decreased again and the patient continues the exercise regime.

It is also desirable to know the angle of rotation the patient was able to achieve. Many such patients have sustained injuries that prevent full +/−90 degree rotation.

In other situations, the patient may be limited in how far he or she should rotate.

SUMMARY

It is desirable that patients or therapists can easily change the "effective" weight of the exercise. In this manner, the patient can strengthen with higher effective weights. By knowing how much "effective" weight the patient is using, improvements can be tracked.

It is therefore desirable that the device be able to quickly change "effective" weight. As patients exercise and rotation angles improve, it is desirable to be able to compile that information as well as provide feedback to the user as the user performs these exercises. In all cases an angle indicator is needed for the therapist to see the angle the patient was able to rotate their arm/hand.

To advance the state of the art of exercise therapy, in view of the foregoing, the present disclosure relates to a pronation supination wrist deviator exercise device that includes a handle having a proximal portion and a distal portion; a shaft defining a longitudinal axis extending from a proximal end to a distal end; and a head portion having a predetermined weight, the head portion or the handle mounted for relative movement on the shaft between a first position and a second position.

In embodiments, the head portion and the handle on the shaft may define a first distance between the head portion and the distal portion of the handle, wherein the predetermined weight of the head portion represents a first weight, the first weight multiplied by the first distance representing a first effective torque of the pronation supination wrist deviator exercise device, and wherein the distance between the head portion and the distal portion of the handle is changed to at least a second distance, the first weight multiplied by the at least a second distance representing at least a second effective torque of the pronation supination wrist deviator exercise device.

In embodiments, the head portion and the handle on the shaft may define a first distance between the head portion and the distal portion of the handle, wherein the predetermined weight of the head portion is changed to at least a second weight, the at least a second weight multiplied by the first distance representing at least a second effective torque of the pronation supination wrist deviator exercise device.

In embodiments, the head portion and the handle on the shaft may define at least a second distance between the head portion and the distal portion of the handle, wherein the predetermined weight of the head portion is at least a second weight, the at least a second weight multiplied by the at least a second distance representing at least another effective torque of the pronation supination wrist deviator exercise device.

In embodiments, the head portion and the handle on the shaft may define at least a second distance between the head portion and the distal portion of the handle, wherein the predetermined weight of the head portion is changed to at least a second weight, the at least a second weight multiplied by the at least a second distance representing at least another effective torque of the pronation supination wrist deviator exercise device.

In embodiments, the handle may further include a manually operable release collar that secures the handle to the shaft, the manually operable release collar enabling a user to secure the handle to and release the handle from various positions on the shaft to adjust distance between the proximal end of the handle and the head portion.

In embodiments, the exercise device may define a central plane through the handle and the head portion and a central line in the central plane extending through the handle and the head portion, wherein the exercise device is positionable by a user at an angle between the central line in the central plane and a vertical line in space, the exercise device further comprising an angle indicator indicating the angle between the central line in the central plane and a vertical line in space at which a user has positioned the exercise device.

In embodiments, the angle indicator may include an angle indicator indicating the angle at which a user has positioned the exercise device when the central plane is parallel to the vertical line in space.

In embodiments, the angle indicator may include an angle indicator indicating the angle at which a user has positioned the exercise device when the central plane is perpendicular to the vertical line in space.

In embodiments, the angle indicator may include an angle indicator indicating the angle at which a user has positioned the exercise device when the central plane is skewed to the vertical line in space.

In embodiments, the angle indicator may be a bubble indicator comprising a plurality of stationary beads circumferentially disposed in a curved path wherein a bubble present in the bubble indicator moves to variable positions indicating the angle between the central line in the central plane and a vertical line in space at which a user has positioned the exercise device.

In embodiments, the exercise device may define a central plane through the handle and the head portion and a central line in the central plane extending through the handle and the head portion, wherein the exercise device is positionable by a user at an angle between the central plane and a vertical line in space, the exercise device further including an angle indicator indicating the angle between the central plane and a vertical line in space at which a user has positioned the exercise device.

In embodiments, the angle indicator may be a bubble indicator that includes a transparent compartment having an outer surface and confining a volume of fluid extending from a portion of the central plane and a plurality of concentric circles disposed on the outer surface wherein a bubble present in the bubble indicator moves to variable positions indicating the angle between the central plane and the vertical line at which a user has positioned the exercise device.

In embodiments, the angle indicator may be a bubble indicator that includes at least one transparent tube having an outer surface and confining a volume of fluid wherein the at least one transparent tube is parallel to the central line in the central plane extending through the handle and the head portion, and wherein a bubble present in the bubble indicator moves to variable positions indicating the angle between the central line in the central plane and a vertical line in space at which a user has positioned the exercise device.

In embodiments, the angle indicator may include at least one transparent tube having an outer surface and confining a volume of fluid wherein the at least one transparent tube defines a curved arc with respect to the central line in the central plane extending through the handle and the head portion, and wherein a bead present in the at least one transparent tube moves to variable positions indicating the angle between the central line in the central plane and a vertical line in space at which a user has positioned the exercise device.

In embodiments, the angle indicator may include at least one transparent tube having an outer surface and confining a volume of fluid wherein the at least one transparent tube defines a circle with respect to the central line in the central plane extending through the handle and the head portion, and wherein an arrow present in the at least one transparent tube points to variable positions within the circle indicating the angle between the central line in the central plane and a vertical line in space at which a user has positioned the exercise device.

In embodiments, the angle indicator may include at least one transparent tube having an outer surface and confining a volume of fluid wherein the at least one transparent tube defines a circle with respect to the central line in the central plane extending through the handle and the head portion, and wherein a bubble present in the at least one transparent tube moves to variable positions indicating the angle between the central line in the central plane and a vertical line in space at which a user has positioned the exercise device.

In embodiments, the exercise device may further include a processor disposed within the exercise device and a memory storing instructions executable by the processor, wherein the instructions when executed by the processor cause the processor to cause an electronically driven arrow to point to variable positions that indicate the angle between the central line in the central plane and a vertical line in space at which a user has positioned the exercise device.

In embodiments, the angle indicator may include a plurality of stationary beads circumferentially disposed around a circle, and the instructions when executed by the processor cause the electronically driven arrow to point to variable positions along the plurality of stationary beads that indicate the angle between the central line in the central plane and a vertical line in space at which a user has positioned the exercise device.

In embodiments, the instructions when executed by the processor cause the processor to digitally indicate the angle between the central line in the central plane and a vertical line in space at which a user has positioned the exercise device.

In embodiments, the exercise device may further include a processor disposed within the exercise device and a memory storing instructions executable by the processor, wherein the instructions when executed by the processor cause the processor to digitally indicate the angle between the central plane and a vertical line in space at which a user has positioned the exercise device.

In embodiments, the instructions when executed by the processor may cause the processor to digitally indicate a horizontal line on the electronic angle indicator that is perpendicular to the central line in the central plane.

In embodiments, the stationary beads may be electrical or electronic lights.

In embodiments, the instructions when executed by the processor may cause the processor to enable electrical communication of measurements of the angle between the central line in the central plane and a vertical line in space at which a user has positioned the exercise device to the processor of a separate electronic device.

In embodiments, the processor may be disposed in an internal volume defined within the head portion.

In embodiments, the processor may be disposed in an internal volume defined within the handle.

In embodiments, the processor may be disposed in an internal volume defined within the head portion.

Again to advance the state of the art of exercise therapy, the present disclosure relates also to a non-transitory computer readable storage medium storing a program which, when executed by a computer, causes the computer to perform a method for setting numerical values relating to a therapeutic exercise program for a user via an exercise device that includes a handle having a proximal portion and a distal portion; a shaft defining a longitudinal axis extending from a proximal end to a distal end; and a head portion having a predetermined weight, the head portion or the handle mounted for relative movement on the shaft between a first position and a second position, wherein the method includes setting as a reference a vertical line in space and setting maximum torque and angle motion levels compared to the reference vertical line.

BRIEF DESCRIPTION OF THE DRAWINGS

The advantages and features of the present disclosure will become more appreciated and better understood when considered in conjunction with the drawings.

DETAILED DESCRIPTION

Figure 1:
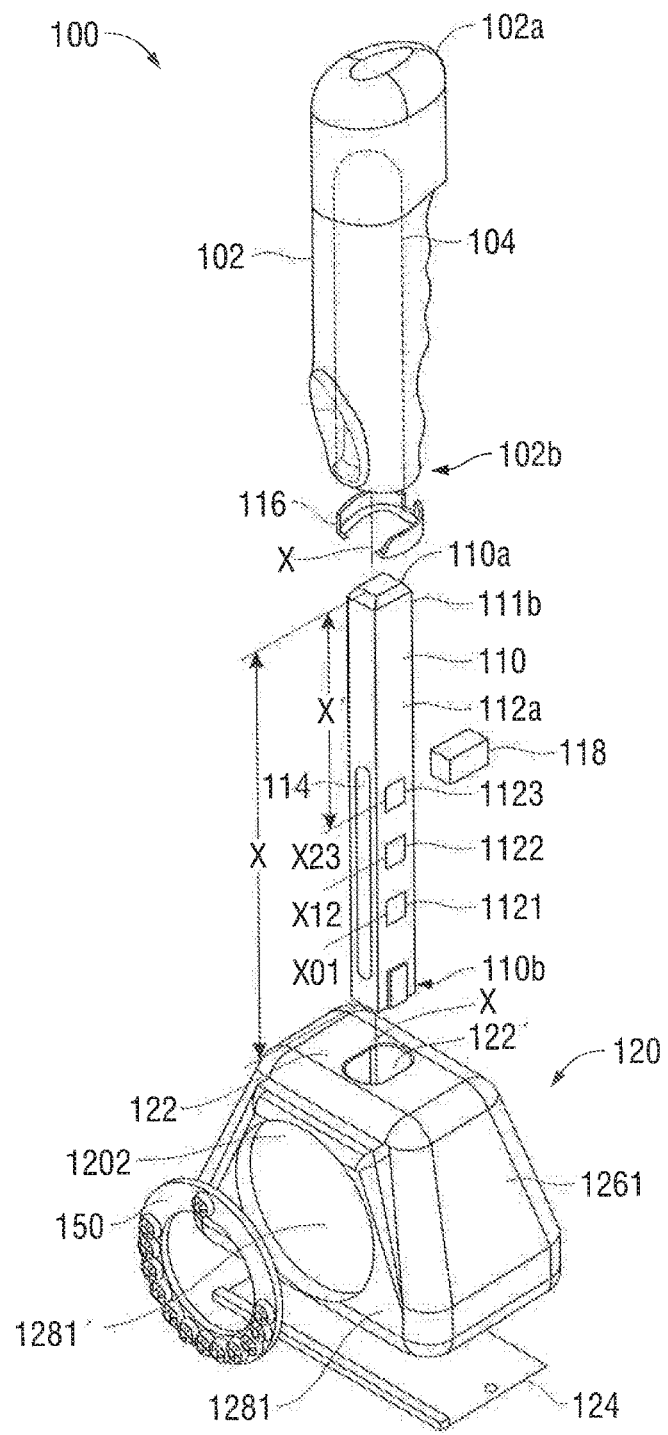
FIG. 1 is an exploded view of an exercise device generally configured in the form of a hammer according to embodiments of the present disclosure.
Figure 2:
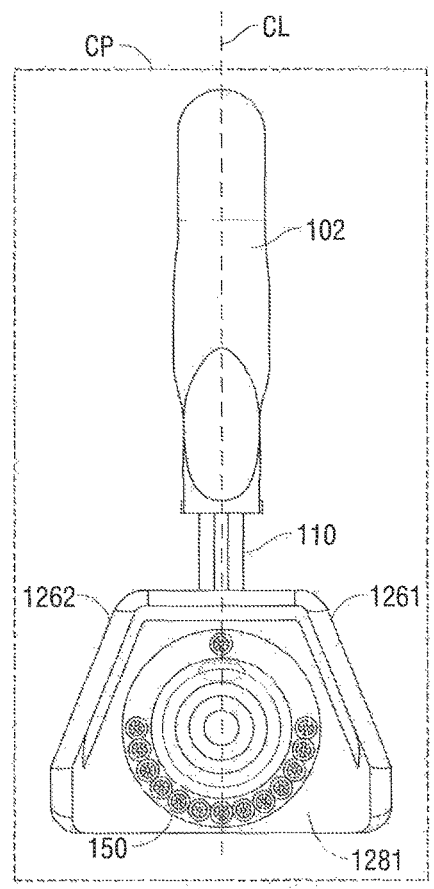
FIG. 2 is front view of the exercise device of FIG. 1 illustrating that the exercise device defines a central plane through the handle and the head portion and a central line in the central plane extending through the handle and the head portion.
Figure 3:
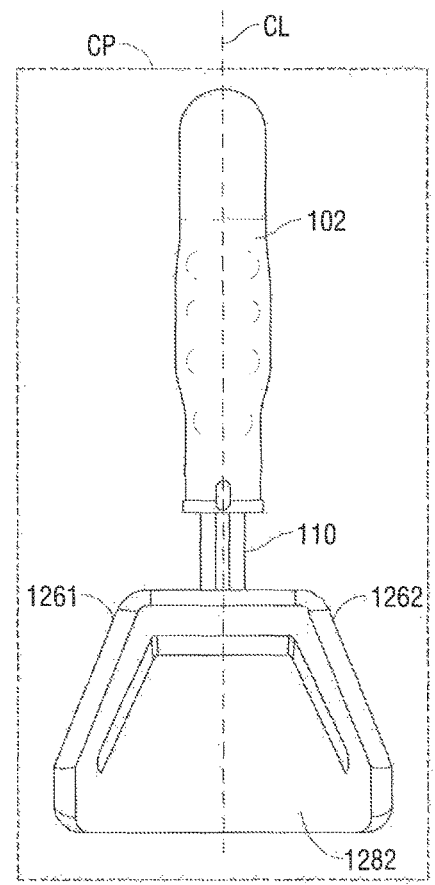
FIG. 3 is front view of the exercise device of FIG. 2 illustrating that the exercise device defines a central plane through the handle and the head portion and a central line in the central plane extending through the handle and the head portion.
Figure 4:
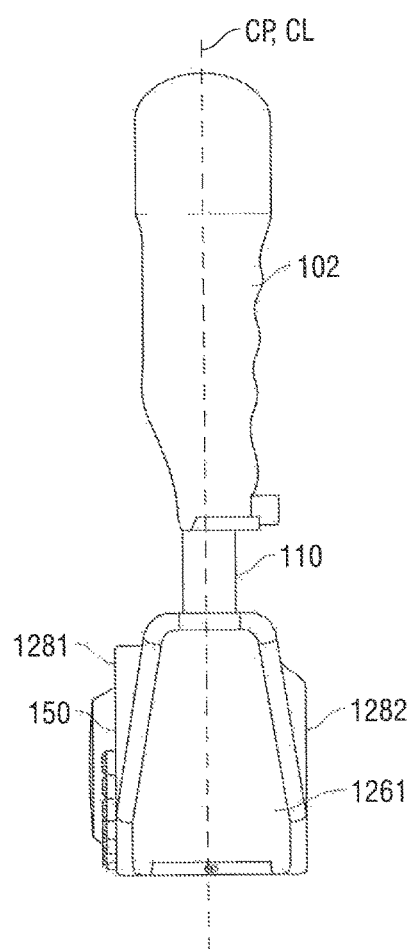
FIG. 4 is a right side view of the exercise device of FIGS. 1-3 illustrating that the exercise device defines a central plane through the handle and the head portion and a central line in the central plane extending through the handle and the head portion.
Figure 5:
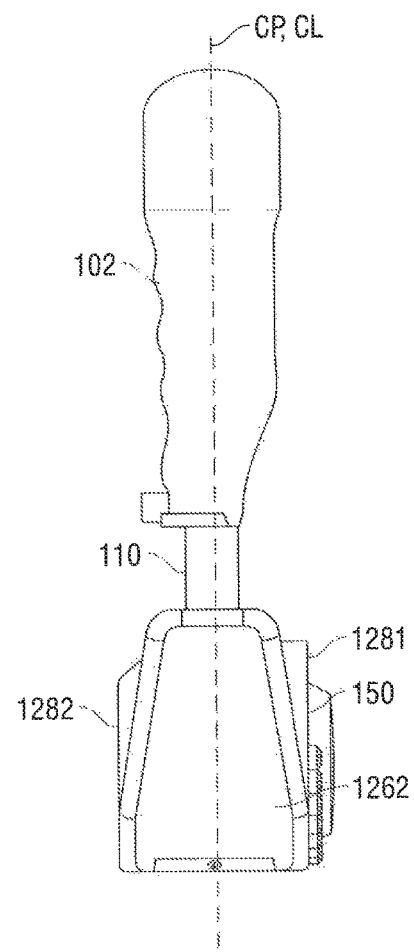
FIG. 5 is a right side view of the exercise device of FIGS. 1-4 illustrating that the exercise device defines a central plane through the handle and the head portion and a central line in the central plane extending through the handle and the head portion.

In the specification and in the accompanying drawings, reference is made to particular features (including method steps or acts) of the present disclosure. It is to be understood that the disclosure in this specification includes combinations of parts, features, or aspects disclosed herein. For example, where a particular feature is disclosed in the context of a particular aspect or embodiment of the present disclosure, or a particular claim, that feature can also be used, to the extent possible, in combination with and/or in the context of other particular aspects and embodiments of the present disclosure, and in the disclosure generally.

Where reference is made herein to a method comprising two or more defined steps or acts, the defined steps or acts can be carried out in any order or simultaneously (except where the context excludes that possibility); and the method can include one or more other steps or acts which are carried out before any of the defined steps or acts, between two of the defined steps or acts, or after all the defined steps or acts (except where the context excludes that possibility).

The term "application" in the disclosed embodiments refers to at least a program designed for end users of a computing device, such as a word processing program, a database program, a browser program, a spreadsheet program, a gaming program, and the like. An application is distinct from systems programs, which consist of low-level programs that interact with the computing device at a very basic level, such as an operating system program, a compiler program, a debugger program, programs for managing computer resources, and the like.

The term "module" may refer to a self-contained component (unit or item) that is used in combination with other components and/or a separate and distinct unit of hardware or software that may be used as a component in a system, such as a wireless or non-wireless communication system. The term "module" may also refer to a self-contained assembly of electronic components and circuitry, such as a stage in a computer that is installed as a unit.

The implementations described herein may be implemented in, for example, a method or a process, an apparatus, a software program, a data stream, or a signal. Even if only discussed in the context of a single form of implementation (for example, discussed only as a method), the implementation of features discussed may also be implemented in other forms (for example, an apparatus or program). An apparatus may be implemented in, for example, appropriate hardware, software, and firmware. The methods may be implemented in, for example, an apparatus such as, for example, a processor, which refers to processing devices in general, including, for example, a computer, a microprocessor, an integrated circuit, or a programmable logic device. Processors also include communication devices, such as, for example, computers, cell phones, tablets, portable/personal digital assistants, and other devices that facilitate communication of information between end-users within a network.

The general features and aspects of the present disclosure remain generally consistent regardless of the particular purpose. Further, the features and aspects of the present disclosure may be implemented in system in any suitable fashion, e.g., via the hardware and software configuration of system or using any other suitable software, firmware, and/or hardware.

For instance, when implemented via executable instructions, various elements of the present disclosure are in essence the code defining the operations of such various elements. The executable instructions or code may be obtained from a readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, readable media may include any medium that may store or transfer information.

The computer means or computing means or processing means may be operatively associated with the stereoscopic system, and is directed by software to compare the first output signal with a first control image and the second output signal with a second control image. The software further directs the computer to produce diagnostic output. Further, a means for transmitting the diagnostic output to an operator of the verification device is included. Thus, many applications of the present disclosure could be formulated. The exemplary network disclosed herein may include any system for exchanging data or transacting business, such as the Internet, an intranet, an extranet, WAN (wide area network), LAN (local area network), satellite communications, and/or the like. It is noted that the network may be implemented as other types of networks.

Additionally, "code" as used herein, or "program" as used herein, may be any plurality of binary values or any executable, interpreted or compiled code which may be used by a computer or execution device to perform a task. This code or program may be written in any one of several known computer languages. A "computer," as used herein, may mean any device which stores, processes, routes, manipulates, or performs like operation on data. A "computer" may be incorporated within one or more transponder recognition and collection systems or servers to operate one or more processors to run the transponder recognition algorithms. Moreover, computer-executable instructions include, for example, instructions and data which cause a general purpose computer, special purpose computer, or special purpose processing device to perform a certain function or group of functions. Computer-executable instructions also include program modules that may be executed by computers in stand-alone or network environments. Generally, program modules include routines, programs, objects, components, and data structures, etc., that perform particular tasks or implement particular abstract data types.

FIG. 1 is an exploded view of a pronation supination wrist-deviator exercise device generally configured in the form of a hammer according to embodiments of the present disclosure.

More particularly, pronation supination wrist deviator exercise device 100 includes a handle 102 having a proximal portion 102*a* and a distal portion 102*b*. Shaft 110 defines a longitudinal axis X-X that extends from a proximal end 110*a* to a distal end 110*b*.

Head portion 120 has a predetermined weight. The head portion 120 or the handle 102 are mounted for relative movement on the shaft 110 between a first position and a second position.

The shaft 110 is illustrated in the form of, for example, a longitudinal rod having a first position 1121 that is distal from the proximal end 110*a*, a second position 1122 that is proximal to the proximal end 110*a* as compared to first position 1121, and a third position 1123 that is still further proximal to the proximal end 110*a* as compared to both first position 1121 and second position 1122. The first, second and third positions 1121, 1122, 1123, respectively, may be represented by notches formed in the shaft 110 at fixed distances between each other.

More particularly, the shaft 110 may have a total length X. Third position 1123 is positioned proximally along axis X-X from proximal end 110*a* a distance X'. Second position 1122 is positioned proximally along axis X-X from third position 1123 a distance $X_{23}$. First position 1121 is positioned proximally along axis X-X from second position 1122 a distance $X_{12}$. Distal end 110*b* of shaft 110 extends a distance $X_{01}$ along axis X-X from first position 1121.

Figure 9:
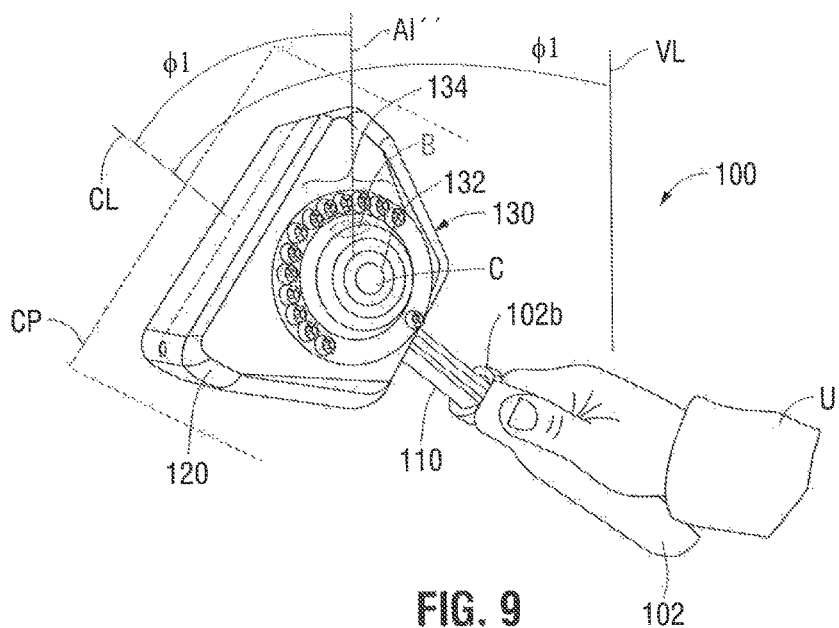
FIG. 9 illustrates the exercise device in a position for pronation-supination exercises.
Figure 10:
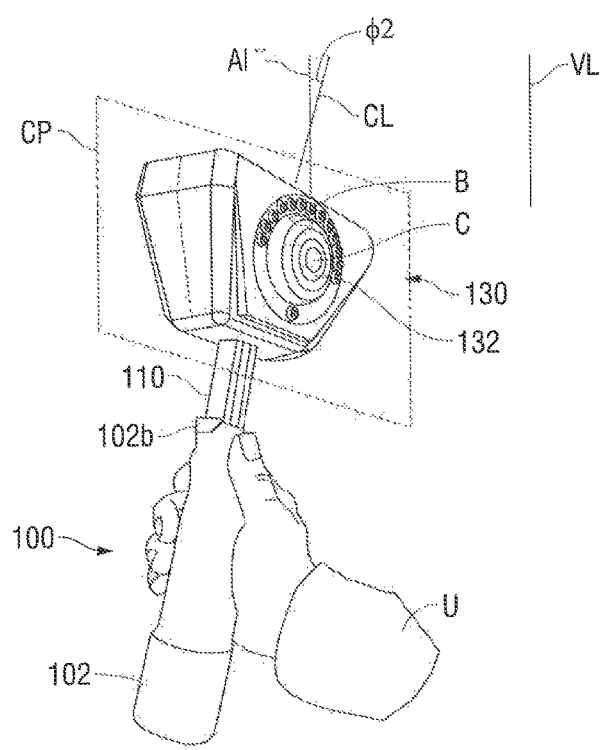
FIG. 10 illustrates the exercise device in another position for pronation-supination exercises.

Head portion 120 defines, in the example embodiment of FIGS. 1-6, a flat-topped pyramidal configuration having six major sides wherein proximal flat surface 122 and distal flat surface 124 (See FIGS. 9 and 10) are disposed parallel to one another and each orthogonally disposed with respect to axis X-X of the shaft 110. The six major sides, which include, in addition to proximal flat surface 122 and distal flat surface 124, tapered lateral opposing sides 1261 and 1262, and front surface 1281 and rear surface 1282, define an internal volume 1202. Distal end 110b of shaft 110 is received through an aperture 122' formed in proximal flat surface 122 that enables access to the internal volume 1202 such that the shaft 110 can be advanced and retracted into and out of the internal volume 1202 in the direction of axis X-X. Additionally, distal flat surface 124 may be formed in the configuration of a removable rectangular plate that also enables access to the internal volume 1202.

In one embodiment, the distal end 110b of the shaft 110 is secured to the head portion 120 by being force fitted into the internal volume 1202 through the aperture 122'. The distal end 110b may be further secured to the head portion 120 within the internal volume 1202 via an adhesive material, e.g., cement that is utilized for weighting of the head portion 120, as described below. In one embodiment, the weight of the head portion 120 may be increased or decreased by the addition or subtraction, respectively, of material (not shown) inside the internal volume 1202. The addition or subtraction of the material may be effected by removal of the distal flat surface or plate 124 to access the internal volume 1202. The material utilized may include a cement or cast iron or other suitable material used for weighting such as in lamp bases, etc.

The head portion 120, the shaft 110 and handle 102 may be made from a metal such as various grades of steel. Alternatively, a hard plastic such as PVC-polycarbonate, such as Palruf™ available from Palm Americas, Inc., Kutztown, Pa., USA, may be employed with a metal reinforcing rod embedded in the shaft 110 (for support). The handle 102 may be coated with thermoplastic elastomer (TPE) rubber which is a non-allergen type rubber available from, e.g., Polyone, Inc., Avon Lake, Ohio, USA, or coated with silicone.

In one embodiment, the distal end 110b of the shaft 110 is removably positioned in the internal volume 1202 to enable changing of the head portion 120 and thus changing of the weight of the head portion 120 by substituting one head portion 120 with another head portion having a different weight.

In a similar manner as described above, also when the distal end 110b of the shaft 110 is removably positioned in the internal volume 1202, the weight of the head portion 120 may be increased or decreased by the addition or subtraction, respectively, of material (not shown) inside the internal volume 1202. The addition or subtraction of the material may be effected by removal of the distal flat surface or plate 124 to access the internal volume 1202.

The shaft 110 defines a channel or groove 114 in a side 111a of the shaft in the direction of the front surface 1281 of head portion 120 and which extends in the direction of axis X-X to at least span the distances $X_{12}$ and $X_{23}$. The first, second and third positions 1121, 1122 and 1123, respectively, are positioned along axis X-X either on lateral side 112a of shaft 110 facing the direction of lateral side 1261 or facing the direction of lateral side 1262 of head portion 120.

The handle 102 further defines an internal volume 104 to which access is enabled via an aperture 102' formed at distal end 102b of the handle 102 that is configured to receive therein proximal end 110a of the shaft 110 and the portion of the shaft that spans the various distances X', $X_{12}$ and $X_{23}$. The handle 102 includes a manually operable release collar 116 that engages with a rod-shaped button 118 that engages within the channel 114 to secure the position of the shaft 110 with respect to first, second and third positions 1121, 1122 and 1123, respectively.

Thus, the manually operable release collar 116 secures the handle 102 to the shaft 110, thereby enabling a user to secure the handle 102 to and release the handle 102 from various positions on the shaft to adjust distance, e.g., various distances X', $X_{12}$ and $X_{23}$, between the proximal end 102a of the handle 102 and the head portion 120.

Front surface 1281 of the head portion 120 further defines an aperture 1281', illustrated in the example of FIG. 1 as a circular aperture, that is configured to receive an angle indicator gauge plate 150. The design of the entire angle indicator is described in more detail with respect to FIGS. 2 and 7-12 which follow below.

FIGS. 2-5 illustrate that the exercise device 100 defines a central plane CP through the handle 102 and the head portion 120 and a central line CL in the central plane CP extending through the handle 102 and the head portion 120.

Figure 6:
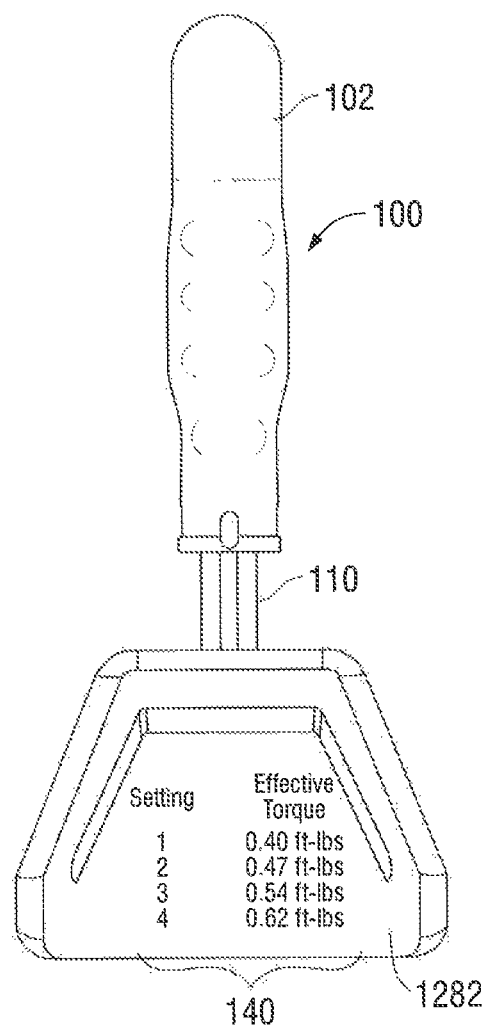
FIG. 6 illustrates the rear side of the exercise device wherein various numbers for "Setting", e.g., 1, 2, 3, 4, may be displayed opposite "Effective Torque"
Figure 7:
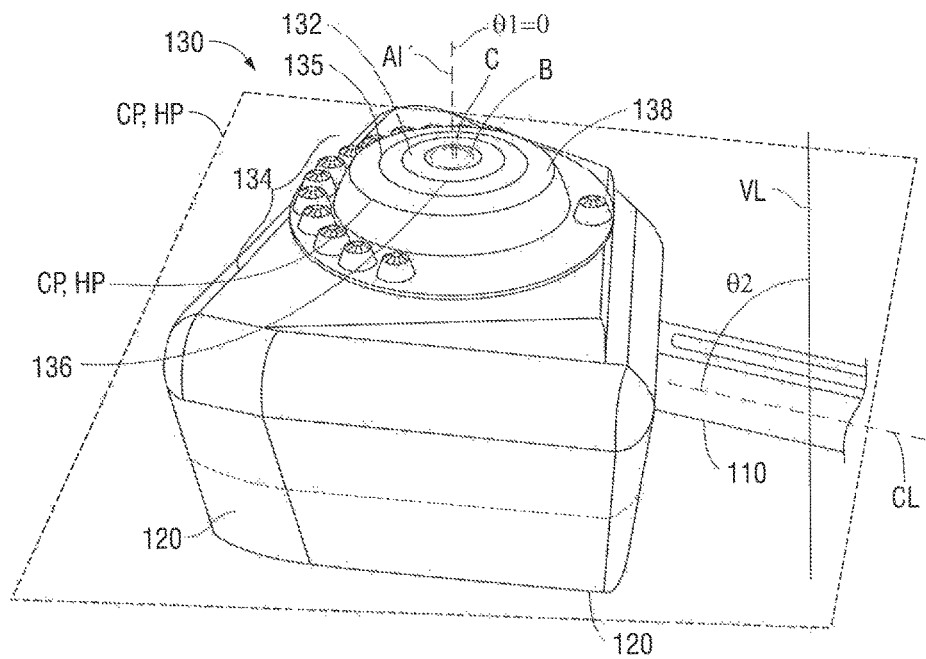
FIG. 7 illustrates a partial view of the exercise device in a position for wrist deviator exercises.

FIG. 6 illustrates the rear side 1282 of the exercise device 100 wherein various numbers for "Setting", e.g., 1, 2, 3, 4, may be displayed opposite "Effective Torque", e.g. 0.40 ft-lbs, 0.47 ft-lbs, 0.54 ft-lbs and 0.62 ft-lbs. The settings and effective torque are described below.

Figure 11A:
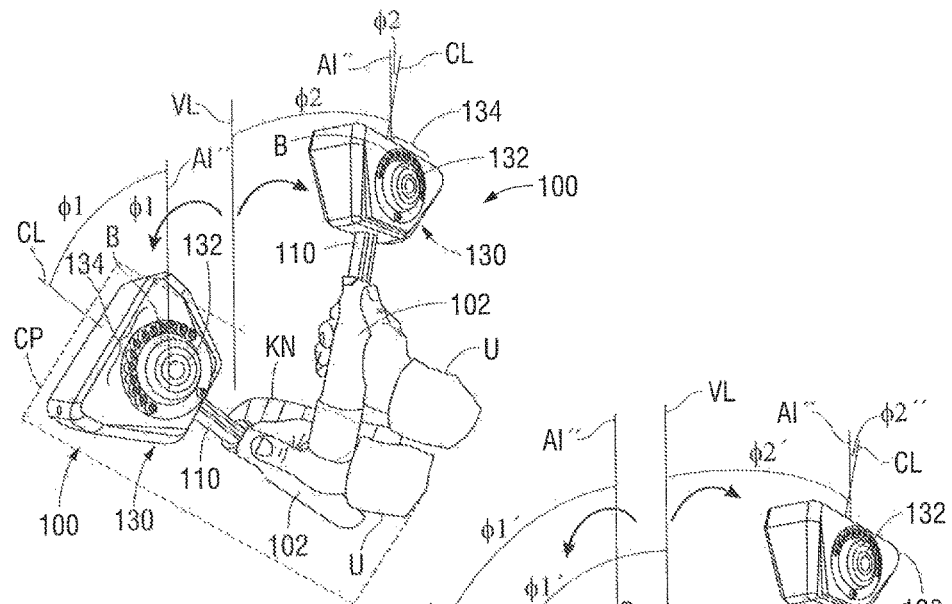
FIG. 11A illustrates the exercise device held and manipulated by a user in a first position wherein an angle is formed between the vertical lime and the central line as the user maintains his or her elbow on his or her knee while the user is in a sitting position for pronation-supination exercises.

Referring now to FIGS. 9, 10, 11A and 11B, the exercise device 100 is positionable by a user at various angles between the central line CL in the central plane CP and a vertical line VL in space. In FIG. 11A, the exercise device 100 is held and manipulated by a user U in a first position wherein an angle $\Phi 1$ is formed between the vertical lime VL and the central line CL as the user U maintains his or her elbow on his or her knee KN while the user U is in a sitting position. Angles $\Phi 1$ and $\Phi 2$ are also formed between the vertical line in space VL and vertical line in space AI" drawn through bubble B in angle indicator 130, discussed further below, and which is parallel to the vertical line VL in space. The user U can also put his or her elbow and forearm on a table so as not to use the shoulder. The exercise device 100 is then held and manipulated by the user U to a second position wherein an angle $\Phi 2$ is formed between the vertical lime VL and the central line CL.

Figure 11B:
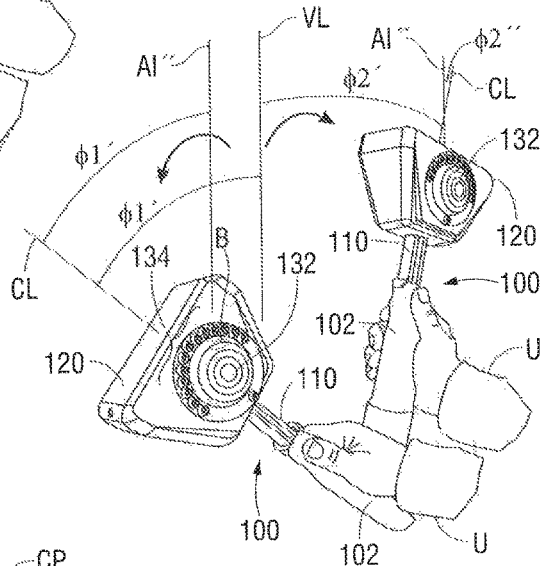
FIG. 11B illustrates the exercise device held and manipulated by a user in a first position wherein now another angle is formed between the vertical line and the central line while the user is in a standing position and the user holds his or her elbow straight out forward for pronation-supination exercises.

In FIG. 11B, the exercise device 100 is also held and manipulated by user U in a first position wherein now an angle $\Phi 1'$ is formed between the vertical line VL and the central line CL while the user U is in a standing position and the user U holds his or her elbow straight out forward. The exercise device 100 is then held and manipulated by the user U to a second position wherein an angle $\Phi 2'$ is formed between the vertical lime VL and the central line CL. These exercises are called pronation and supination. As a result, the angle indicator 130 indicates one or more angles $\Phi 1$, $\Phi 2$, $\Phi 1'$ or $\Phi 2'$ at which the user U has positioned the exercise device 100 when the central plane CP may be parallel to the vertical line VL in space. In a similar manner, angles $\Phi 1'$ and $\Phi 2'$ are also formed between the vertical line in space VL and vertical line in space AI" drawn through bubble B in angle indicator 130, discussed further below, and which is parallel to the vertical line VL in space.

Figure 12:
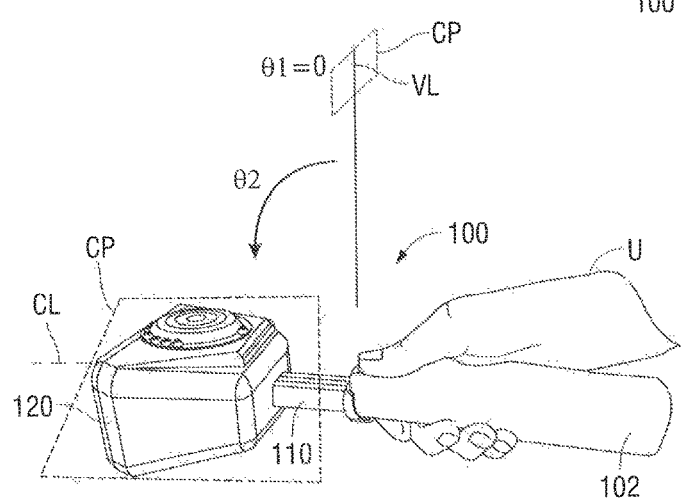
FIG. 12 illustrates the exercise device being positionable by a user at various angles between the central plane and the vertical line in space for wrist deviator exercises.

In FIG. 12, the exercise device 100 is positionable by user U at various angles between the central plane CP and the vertical line VL in space. More particularly, the exercise device 100 is held and manipulated by user U between a first position, not shown, wherein the central plane CP and the vertical line VL are parallel, as indicated by angle θ1, to a second position, as shown, wherein the central plane CP and the vertical line VL are perpendicular to one another, as indicated by angle θ2. These exercises are called wrist deviator exercises.

As illustrated also in FIGS. 2 and 7-10, as described above, the exercise device 100 further includes angle indicator 130 indicating the angle between the central line CL in the central plane CP and the vertical line VL in space at which a user U has positioned the exercise device 100.

The angle indicator 130 may be a bubble indicator 132 that includes a plurality of stationary beads 134 of different colors circumferentially disposed in a curved path wherein bubble B present in the bubble indicator 132 moves to variable positions wherein via a vertical line in space AI' drawn through the bubble B in the bubble indicator 132, and which is parallel to the vertical line VL, enables indicating the angles Φ1, Φ2 and Φ1', Φ2' between the central line CL in the central plane CP and the vertical line VL in space at which the user U has positioned the exercise device 100.

Returning to FIGS. 7 and 8 in conjunction with FIG. 12, FIG. 7 illustrates a partial view of the exercise device 100 in the position shown in FIG. 12 for wrist deviator exercises. More particularly, in FIG. 7, the central plane CP of the exercise device 100 is coincident with a reference horizontal plane HP that is perpendicular to the reference vertical line VL in space.

A reference angle indicator line AI' is drawn through the center C of the bubble indicator 132 and which is perpendicular to the central plane CP and, for the position shown, the angle indicator line AI' is perpendicular to the reference horizontal plane HP. Therefore, the angle θ1 in FIG. 12 is zero since the angle indicator line AI' and the reference vertical line VL are parallel to one another. Therefore, the bubble B gravitates to the center C of the bubble indicator 132. Accordingly, the angle indicator 130 indicates angle θ1 at which a user has positioned the exercise device 100 when the central plane CP is perpendicular to the vertical line VL in space.

Thus, the bubble indicator 132 includes a plurality of stationary beads 134 circumferentially disposed in a curved path wherein a bubble B present in the bubble indicator 132 moves to variable positions indicating the angle between the central line CL in the central plane CP and vertical line VL in space at which a user has positioned the exercise device 100.

Figure 8:
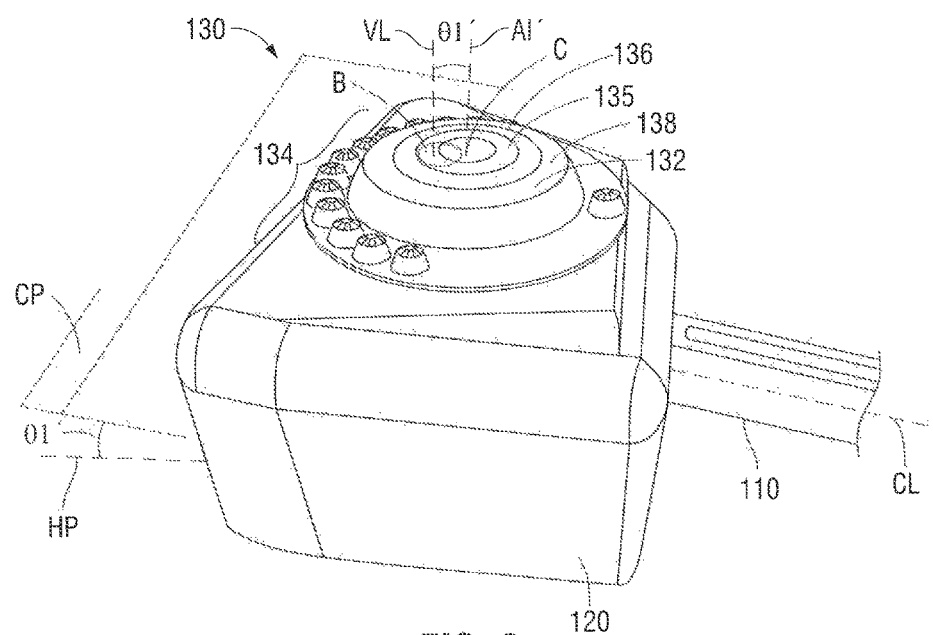
FIG. 8 illustrates another partial view of the exercise device in a position for wrist deviator exercises.

In FIG. 8, the exercise device 100 is held and manipulated by a user such that the central plane CP is tilted at an angle θ1' with respect to the horizontal plane HP. The reference vertical line VL, which is still perpendicular to the horizontal plane HP, may now be considered to pass through the center of the bubble B, which has now shifted away from the center C of the bubble indicator 132. Accordingly, the angle indicator line AI' and the reference vertical line VL also form the angle θ1' with respect to each other. Since the bubble indicator 132 includes a plurality of concentric circles 136 with respect to the center C of the bubble indicator 132, the angle θ1' may be approximately read by determining to which concentric circle the bubble B shifts. Thus, the angle indicator 130 indicates angle θ1' at which a user has positioned the exercise device 100 when the central plane CP is skewed to the vertical line VL in space.

The bubble indicator 132 includes a transparent compartment 135 having an outer surface and confining a volume of fluid 138 extending from a portion of the central plane CP and the plurality of concentric circles 136 disposed on the outer surface wherein the bubble B present in the bubble indicator 132 moves to variable positions indicating the variable angles θ1, θ1' and θ2 between the central plane CP and the vertical line VL at which a user has positioned the exercise device.

FIGS. 13A-13D illustrate various configurations of the exercise device 100 to achieve different effective torques. More particularly, in FIG. 13A, the head portion 120 and the handle 102 on the shaft 102 define a first distance D1 between the head portion and the distal portion 102b of the handle 102. The head portion 120 defines a center of gravity 120CG1. When the distal portion of the handle 102b is positioned at its most distal position $X_{01}$, the distal portion of the handle 102b is positioned almost contacting the proximal flat surface 122 to define the distance D1 between the center of gravity 120CG1 of the head portion 120 and the distal portion of the handle 102b. A distance D1' may further be defined between the center of gravity 120CG1 of the head portion 120 and the effective center of gravity 102CG of the shaft 110 and the handle 102b.

The predetermined weight of the head portion 120 represents a first weight W1. The first weight W1 multiplied by the first distance D1 represents a first effective torque T1 of the pronation supination wrist deviator exercise device 100.

Figure 13A:
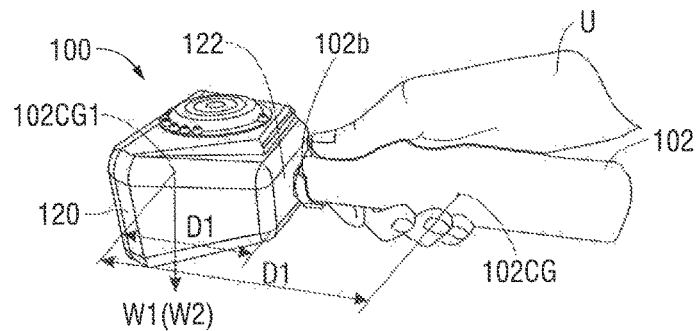
FIG. 13A illustrates the head portion and the handle on the shaft define a first distance between the head portion and the distal portion of the handle to define a first effective torque.
Figure 13B:
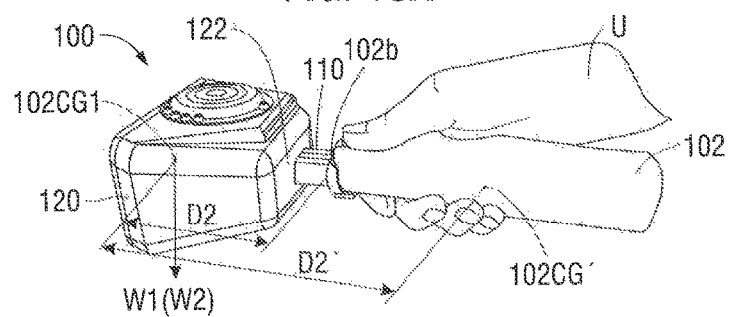
FIG. 13B illustrates the distance between the center of gravity of the head portion and the distal portion of the handle is changed to at least a second distance by adjusting the position of the handle on the shaft to a first proximal position to effect at least at least a second effective torque of the pronation supination wrist deviator exercise device.

Referring to FIG. 13B, the distance D1 between center of gravity 120CG1 of the head portion 120 and the distal portion of the handle 102b is changed to at least a second distance D2, e.g., by adjusting the position of the handle 102b on the shaft 110 to first proximal position 1121. The first weight W1 multiplied by second distance D2 represents at least a second effective torque T2 of the pronation supination wrist deviator exercise device 100.

Thus, the head portion 120, having a predetermined weight W1 or the handle 102 are mounted for relative movement on the shaft 110 between a first position, e.g., as represented by distance D1, and a second position, e.g., as represented by distance D2.

A distance D2' may further be defined between the center of gravity 120CG1 of the head portion 120 and a first shifted effective center of gravity 102CG' of the shaft 110 and the handle 102b.

Figure 13C:
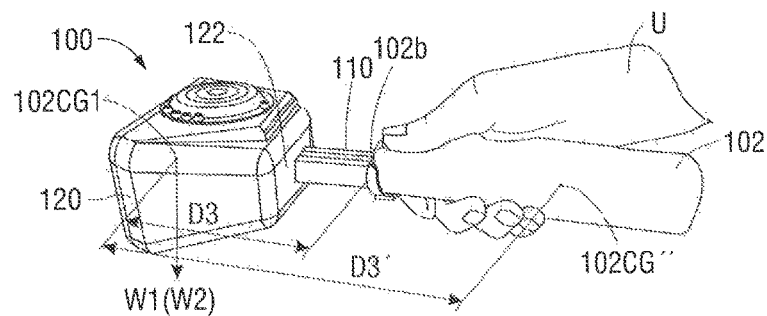
FIG. 13C illustrates the distance between the center of gravity of the head portion and the distal portion of the handle is changed to a third distance to effect a third effective torque of the pronation supination wrist deviator exercise device.

Referring to FIG. 13C, the distance D2 between center of gravity 120CG1 of the head portion 120 and the distal portion of the handle 102b is changed to a third distance D3, e.g., by adjusting the position of the handle 102b on the shaft 110 to second proximal position 1122. The first weight W1 multiplied by third distance D3 represents a third effective torque T3 of the pronation supination wrist deviator exercise device 100.

Thus, the head portion 120, having a predetermined weight W1 or the handle 102 are mounted for relative movement on the shaft 110 between a second position, e.g., as represented by distance D2, and a third position, e.g., as represented by distance D3.

A distance D3' may further be defined between the center of gravity 120CG1 of the head portion 120 and a second shifted effective center of gravity 102CG" of the shaft 110 and the handle 102b.

Figure 13D:
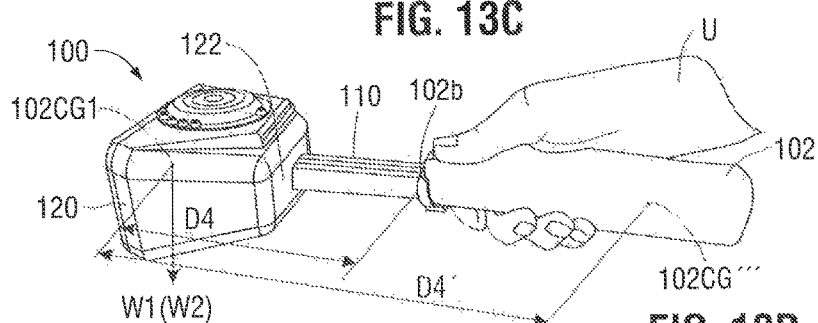
FIG. 13D illustrates the distance between the center of gravity of the head portion and the distal portion of the handle is changed to a fourth distance to effect a fourth effective torque of the pronation supination wrist deviator exercise device.

In FIG. 13D, the distance D3 between 120CG1 of the head portion 120 and the distal portion of the handle 102b is changed to a fourth distance D4, e.g., by adjusting the position of the handle 102b on the shaft 110 to third proximal position 1123. The first weight W1 multiplied by fourth distance D4 represents a fourth effective torque T4 of the pronation supination wrist deviator exercise device 100.

Thus, the head portion 120, having a predetermined weight W1 or the handle 102 are mounted for relative movement on the shaft 110 between a third position, e.g., as represented by distance D3, and a fourth position, e.g., as represented by distance D4.

A distance D4' may further be defined between the center of gravity 120CG1 of the head portion 120 and a third shifted effective center of gravity 102CG''' of the shaft 110 and the handle 102b.

Those skilled in the art will recognize that predetermined weight W1 may be changed to a predetermined second weight W2 and that the effective torques can again be changed by multiplying the second weight W2 by the first, second, third and fourth distances D1, D2, D3 and D4, respectively. The weights may be changed further to third and fourth weights, etc. and additional effective torques can be realized.

Figure 14:
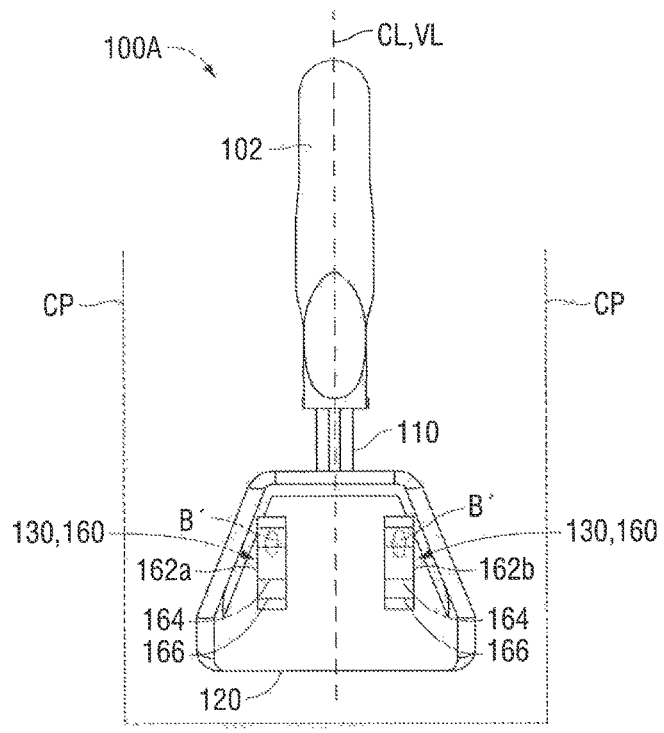
FIG. 14 illustrates an alternate embodiment of the exercise device wherein the angle indicator is a bubble indicator that includes at least one transparent tube and wherein the device is oriented so that the central line in the central plane coincides with the vertical line.
Figure 15:
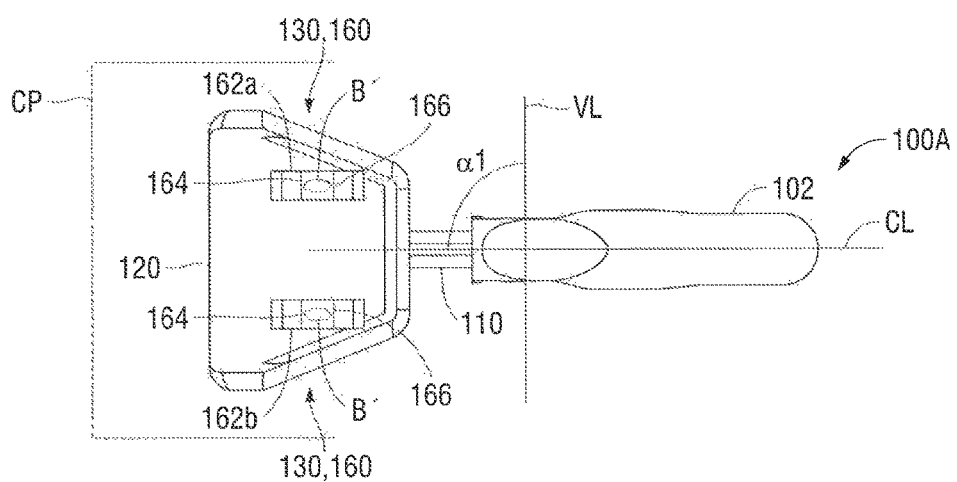
FIG. 15 illustrates the alternate embodiment of the exercise device of FIG. 14 wherein the device is oriented so that the central line in the central plane is perpendicular with respect to the vertical line.

FIGS. 14 and 15 illustrate an exercise device 100A that is identical to exercise device 100 except wherein the angle indicator 130 is a bubble indicator 160 that includes at least one transparent tube, e.g. linearly configured transparent tube 162a and linearly configured transparent tube 162b, having an outer surface with intermittent markings 164 and confining a volume of fluid 166 wherein the one or more transparent tubes 162a and 162b are parallel to the central line CL in the central plane CP extending through the handle 102 and the head portion 120. A bubble present B' in the transparent tubes 162a and 162b of the bubble indicators 160 moves to variable positions represented by the intermittent markings 164 indicating the angle between the central line CL in the central plane CP and a vertical line VL in space at which a user has positioned the exercise device 100A.

In FIG. 14, the exercise device 100A is oriented so that the central line CL in the central plane CP coincides with the vertical line VL so the angle between the two lines is zero. Therefore, the bubbles B' in the transparent tubes 162a and 162b rise to the proximal end of the tubes.

In FIG. 15, the exercise device 100A is oriented so that the central line CL in the central plane CP is perpendicular with respect to the vertical line VL so the angle α1 between the two lines is 90°. Therefore, the bubbles B' in the transparent tubes 162a and 162b stabilize in the center of the tubes.

Figure 16:
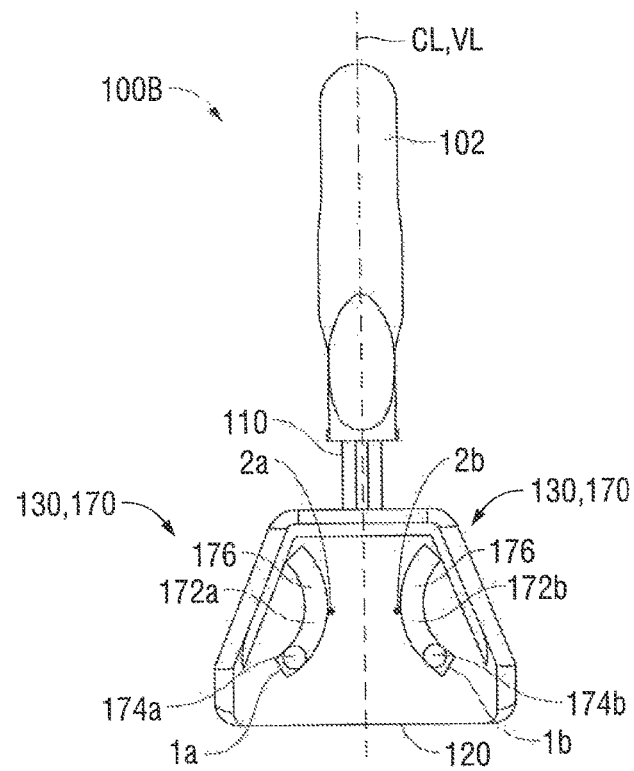
FIG. 16 illustrates another alternate embodiment of the exercise device wherein the angle indicator again includes at least one transparent tube but which defines a curved arc containing a bead wherein the device is oriented so that the central line in the central plane coincides with the vertical line.
Figure 17:
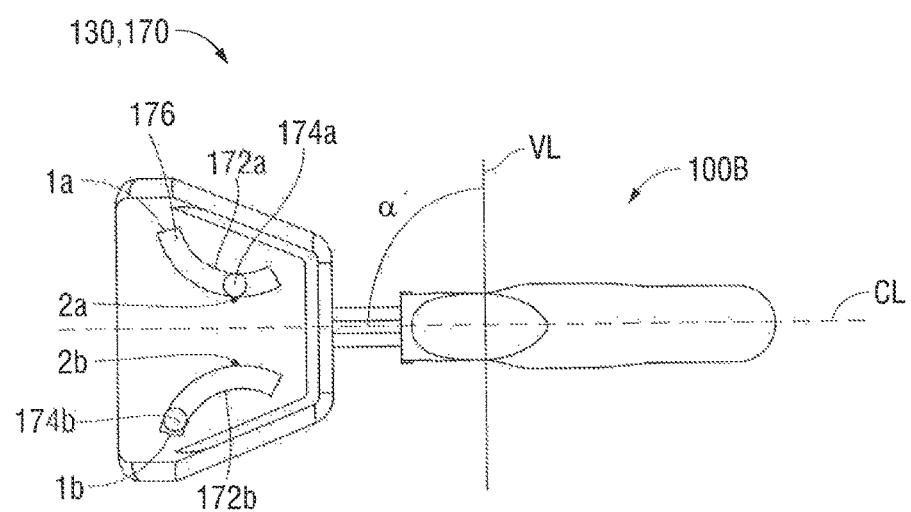
FIG. 17 illustrates the alternate embodiment of the exercise device of FIG. 16 wherein the device is oriented so that the central line in the central plane is perpendicular with respect to the vertical line.

FIGS. 16 and 17 illustrate another exercise device 100B that is also identical to exercise device 100 except wherein the angle indicator 130 is a bubble indicator 170 that again includes at least one transparent tube but which defines a curved arc, e.g., curved arc transparent tube 172a and curved arc transparent tube 172b, having an outer surface and confining a volume of fluid 176 wherein the one or more transparent tubes 172a and 172b are disposed on opposite sides of the central line CL in the central plane CP extending through the handle 102 and the head portion 120. Instead of a bubble B' as is present in the transparent tubes 162a and 162b of the bubble indicators 160, beads 174a and 174b in tubes 172a and 172b, respectively, move to variable positions again indicating the angle between the central line CL in the central plane CP and a vertical line VL in space at which a user has positioned the exercise device 100B. Transparent tube 172a has a distal end 1a and a position 2a that is closest to the central line CL. Similarly, transparent tube 172b has a distal end 1b and a position 2b that is closest to the central line CL. Thus, the one or more transparent tubes 172a and 172b define a curved arc with respect to the central line CL in the central plane CP extending through the handle 102 and the head portion 120.

In FIG. 16, the exercise device 100B is oriented so that the central line CL in the central plane CP coincides with the vertical line VL so the angle between the two lines is zero. Therefore, the beads 174a and 174b fall to the distal ends 1a and 1b of the transparent tubes 172a and 172b, respectively.

In FIG. 17, the exercise device 100B is oriented so that the central line CL in the central plane CP is perpendicular with respect to the vertical line VL so the angle α1' between the two lines is 90°. Therefore, the bead 174a in the transparent tube 172a falls to the lowest position of the tube, i.e., to position 1a which is closest to the central line C, while the bead 174b falls to the distal end 1b of transparent tube 172b.

Therefore, variable positions and angles α1' can be measured via the angle indicator 170.

Figure 18:
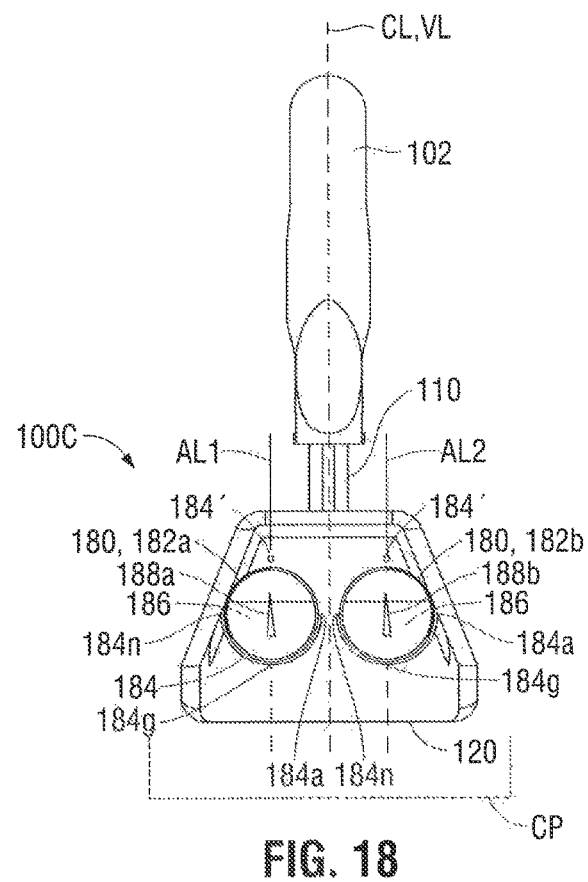
FIG. 18 illustrates still another alternate embodiment of the exercise device wherein the angle indicator that includes at least one transparent tube and an arrow present in the tubes points to variable positions within the circle indicating the angle between the central line in the central plane and vertical line in space at which a user has positioned the exercise device and wherein the device is oriented so that the central line in the central plane coincides with the vertical line.
Figure 19:
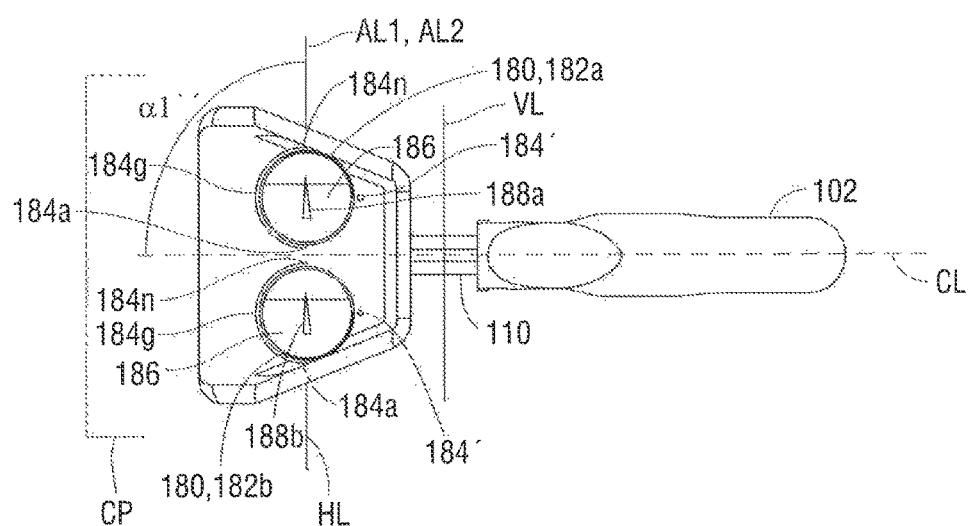
FIG. 19 illustrates the alternate embodiment of the exercise device of FIG. 18 wherein the device is oriented so that the central line in the central plane is perpendicular with respect to the vertical line.

FIGS. 18 and 19 illustrate still another exercise device 100C that is also identical to exercise device 100 except wherein the angle indicator 130 is a bubble indicator 180 that includes at least one transparent tube, e.g., transparent tubes 182a and 182b, each having an outer surface confining a volume of fluid 186 wherein the transparent tubes 182a and 182b each defines a circle with respect to the central line CL in the central plane CP extending through the handle 102 and the head portion 110. An arrow present in the one or more transparent tubes 182a and 182b, e.g., arrow 188a in transparent tube 182a and arrow 188b in transparent tube 188b, points to variable positions within the circle indicating the angle α1'' between the central line CL in the central plane CP and vertical line VL in space at which a user has positioned the exercise device 100C. More particularly, the angle indicators 182a and 182b each include a circular arc extending 180° from position 184a to position 184n.

In FIG. 18, the exercise device 100C is in a vertical position with the handle 102 above the head portion 120 whereas in FIG. 19, the handle 102 and the shaft 110 are in a horizontal position. More particularly, in FIG. 18, the handle 102, the shaft 110 and the head portion 120 are in a vertical position wherein the handle 102 is above the head portion 120 and such that the central line CL in the central plane CP is aligned with the vertical line in space VL.

The circular arc extending circumferentially disposed in a curved path around the bubble indicators 182a and 182b each further includes a stationary bead 184' that is disposed at the proximal most position of the circular bubble angle indicators 182a and 182b and in alignment with the central line CL.

When the handle 102, the shaft 110 and the head portion 120 are in the vertical position wherein the handle 102 is above the head portion 120 and such that the central line CL in the central plane CP is aligned with the vertical line in space VL as illustrated in FIG. 18, the arrows 188a and 188b each remain at a position immediately below and aligned with the stationary bead 184 and the central line CL. Accordingly, the angles Φ1 and Φ2 that are illustrated in FIGS. 9, 10, 11A and 11B are equal to 180°.

In FIG. 19, the handle 102, the shaft 110 and the head portion 120 are in a horizontal position wherein the handle 102 is above the head portion 120 and such that the central line CL in the central plane CP is perpendicular to the vertical line in space VL. As noted, the circular arc extending circumferentially disposed in a curved path around the bubble indicators 182a and 182b extend in an arc of 180° on the periphery of the distal semi-circular portion of the angle indicators 182a and 182b wherein a line HL drawn across the angle indicators 182a and 182b from positions 184a to 184n is perpendicular to the central line CL and position 184g is aligned with the central line CL. Thus, the arcs defined by positions extending from 184a to . . . 184g and from 184g to . . . 184n are each 90° wherein the positions 184a and 184n are each at the most extreme lateral positions from central line CL.

When the handle 102, the shaft 110 and the head portion 120 are in the horizontal position illustrated in FIG. 19, the fluid level remains perpendicular with respect to the vertical line VL such that the arrows 188*a* and 188*b* each point to a position immediately below the most extreme position 184*n* of each angle indicator 182*a* and 182*b*. Accordingly, angle α1″ between the central line CL and the vertical line in space VL is equal to 90°. Thus, the arrows 188*a* and 188*b* will always point upwards in parallel to the vertical line in space VL. The arcs always move as the exercise device 100C is moved while the level of the fluid 186 remains perpendicular to the vertical line VL.

Figure 20:
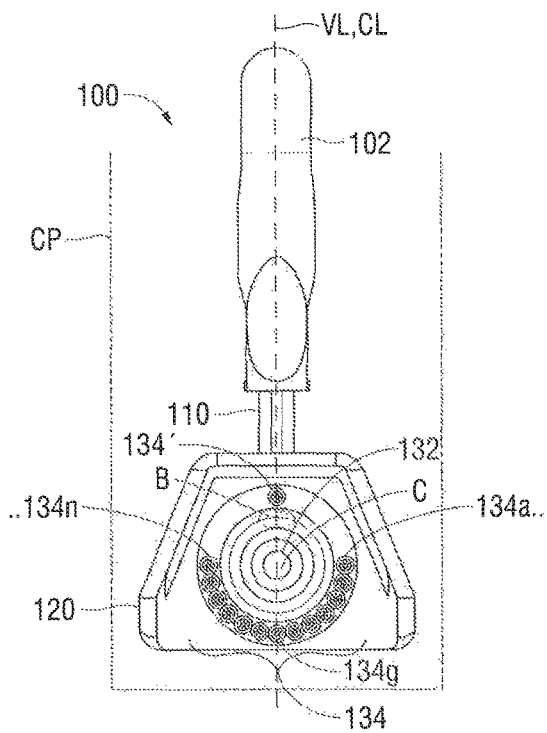
FIG. 20 illustrates the exercise device of FIGS. 1-13D in a vertical position with the handle above the head portion.
Figure 21:
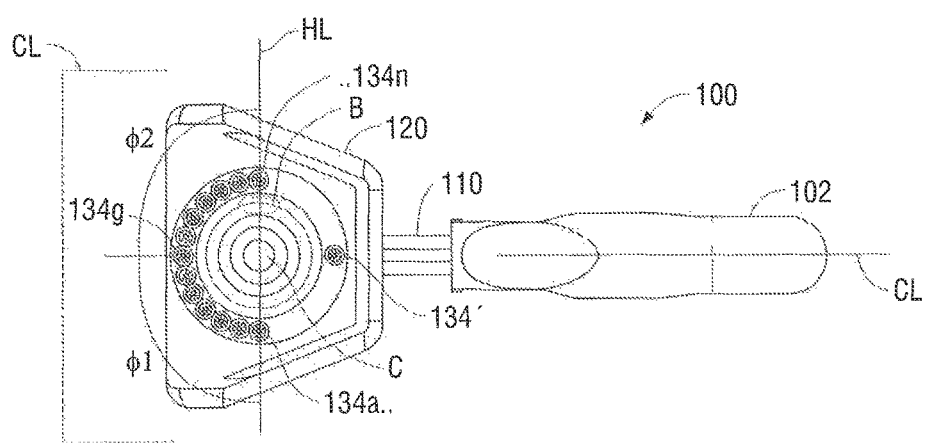
FIG. 21 illustrates the exercise device of FIGS. 1-13D in a horizontal position.

FIGS. 20 and 21 illustrate the exercise device 100 that has been described above with respect to FIGS. 1-13D in a vertical position with the handle 102 above the head portion 120 and in a horizontal position, respectively. More particularly, in FIG. 20, the handle 102, the shaft 110 and the head portion 120 are in a vertical position wherein the handle 102 is above the head portion 120 and such that the central line CL in the central plane CP is aligned with the vertical line in space VL.

The plurality of stationary beads 134 of different colors circumferentially disposed in a curved path around the bubble indicator 130 further includes a stationary bead 134' that is disposed at the proximal most position of the circular bubble angle indicator 130 and in alignment with the central line CL.

When the handle 102, the shaft 110 and the head portion 120 are in the vertical position wherein the handle 102 is above the head portion 120 and such that the central line CL in the central plane CP is aligned with the vertical line in space VL as illustrated in FIG. 20, the bubble B shifts and stabilizes at a position immediately below and aligned with the stationary bead 134 and the central line CL. Accordingly, the angles Φ1 and Φ2 that are illustrated in FIGS. 9, 10, 11A and 11B are equal to 180°.

In FIG. 21, the handle 102, the shaft 110 and the head portion 120 are in a horizontal position wherein the handle 102 is above the head portion 120 and such that the central line CL in the central plane CP is perpendicular to the vertical line in space VL. The plurality of concentric beads 134 on the bubble angle indicator 130 extend in an arc of 180° on the periphery of the distal semi-circular portion of the angle indicator 130 to include beads 134*a* . . . 134*n* wherein a line HL drawn across the angle indicator 130 from bead 134*a* to bead 134*n* is perpendicular to the central line CL and bead 134*g* is aligned with the central line CL. Thus, the arcs defined by beads 134*a* to . . . 134*g* and beads 134*g* to . . . 134*n* are each 90° and the beads 134*a* and 134*n* each at the most extreme lateral position from central line CL.

When the handle 102, the shaft 110 and the head portion 120 are in the horizontal position illustrated in FIG. 21, the bubble B rises to a position immediately below the most extreme bead 134*n*. Accordingly, the angles Φ1 and Φ2 that are illustrated in FIGS. 9, 10, 11A and 11B are equal to 90°.

FIGS. 20 and 21 illustrate the exercise device 100 that has been described above with respect to FIGS. 1-13D in a vertical position with the handle 102 above the head portion 120 and in a horizontal position, respectively. More particularly, in FIG. 20, the handle 102, the shaft 110 and the head portion 120 are in a vertical position wherein the handle 102 is above the head portion 120 and such that the central line CL in the central plane CP is aligned with the vertical line in space VL.

The plurality of stationary beads 134 of different colors circumferentially disposed in a curved path around the bubble indicator 130 further includes a stationary bead 134' that is disposed at the proximal most position of the circular bubble angle indicator 132 and in alignment with the central line CL.

When the handle 102, the shaft 110 and the head portion 120 are in the vertical position wherein the handle 102 is above the head portion 120 and such that the central line CL in the central plane CP is aligned with the vertical line in space VL as illustrated in FIG. 20, the bubble B shifts and stabilizes at a position immediately below and aligned with the stationary bead 134 and the central line CL. Accordingly, the angles Φ1 and Φ2 that are illustrated in FIGS. 9, 10, 11A and 11B are equal to 180°.

In FIG. 21, the handle 102, the shaft 110 and the head portion 120 are in a horizontal position wherein the handle 102 is above the head portion 120 and such that the central line CL in the central plane CP is perpendicular to the vertical line in space VL. The plurality of concentric beads 134 on the bubble angle indicator 130 extend in an arc of 180° on the periphery of the distal semi-circular portion of the angle indicator 130 to include beads 134*a* . . . 134*n* wherein a line HL drawn across the angle indicator 130 from bead 134*a* to bead 134*n* is perpendicular to the central line CL and bead 134*g* is aligned with the central line CL. Thus, the arcs defined by beads 134*a* to . . . 134*g* and beads 134*g* to . . . 134*n* are each 90° and the beads 134*a* and 134*n* each at the most extreme lateral position from central line CL.

When the handle 102, the shaft 110 and the head portion 120 are in the horizontal position illustrated in FIG. 21, the bubble B rises to a position immediately below the most extreme bead 134*n*. Accordingly, the angles Φ1 and Φ2 that are illustrated in FIGS. 9, 10, 11A and 11B are equal to 90°. Thus, if an arrow is drawn from the center C of the angle indicator 130 to the bubble B, the arrow will always point upwards in parallel to the vertical line in space VL. The arc of beads 134*a* . . . 134*n* always moves as the exercise device 100 is moved.

Figure 22:
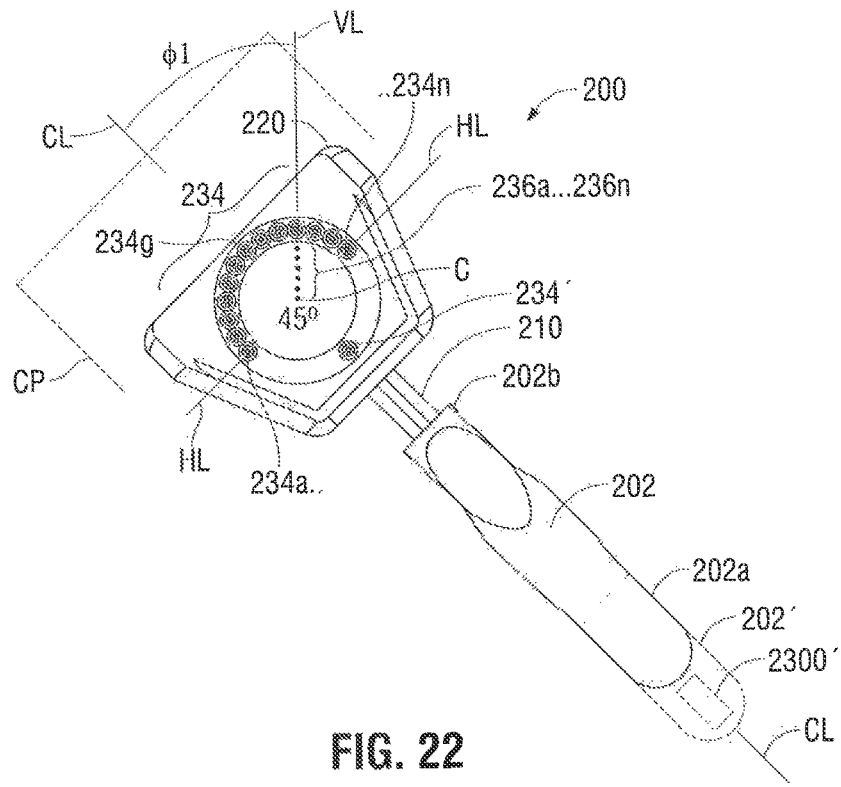
FIG. 22 illustrates another embodiment of the exercise device wherein the angle indicator includes electronic display, settings and measurements features.

FIG. 22 illustrates another embodiment of the exercise device 100 wherein the angle indicator includes electronic display, settings and measurements features. More particularly, exercise device 200 is identical to exercise device 100 described above with respect to FIGS. 1-13D and 20-21 but which now includes an electronic angle indicator 230. In a similar manner as described above with respect to FIGS. 20-21, exercise device 200 includes a handle 202 that is identical to handle 102 of exercise devices 100, 100A, 100B and 100C, a shaft 210 that is identical to shaft 110 and includes the features related to shaft 110 and is not discussed further.

In view of the foregoing description in FIGS. 1-21 of the exercise devices 100, 100A, 100B and 100C, the angle indicator 130 and further represented by mechanical angle indicators 132, 160, 170 AND 180? enable measurement of the variable angles Φ1, Φ1', Φ2, Φ2' between the central line CL in central plane CP and the vertical line VL in space, and further enable measurement of the variable angles θ1, θ1' and θ2 between the central plane CP and the vertical line VL in space at which a user has positioned the exercise device.

Those skilled in the art will also recognize and understand with respect to the foregoing description in FIGS. 1-21 of the exercise devices 100, 100A, 100B and 100C that the mechanical angle indicator 130 and further represented by mechanical angle indicators 160, 170 and 180 enable various methods of therapeutic exercise using the various devices that include mechanical angle indicators and also enable a method of manufacturing the exercise devices 100, 100A, 100B and 100C that includes the mechanical angle indicator 130 and respectively the mechanical angle indicators 160, 170 and 180.

Figure 23:
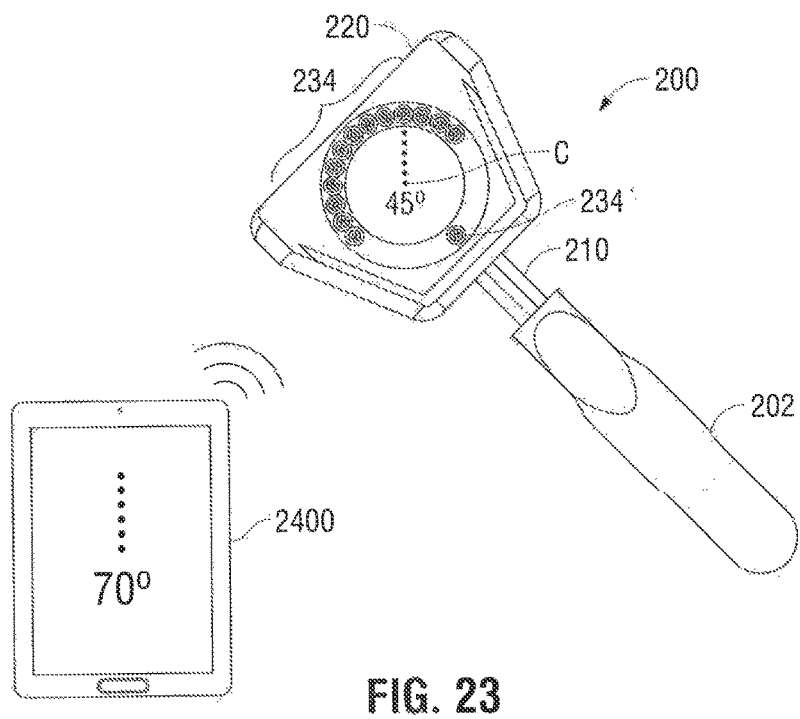
FIG. 23 illustrates the exercise device of FIG. 22 wherein the electronic angle indicator is in electrical communication with an external wireless device.

FIGS. 22-23 illustrate exercise device 200 which is mechanically identical to the exercise devices 100, 100A, 100B and 100C described above except for certain differences that are described below. Those skilled in the art will recognize the similarities between exercise device 200 and exercise devices 100, 100A, 100B and 100C described above, so that only those features of exercise device 200 deemed essential to illustrate differences are described in detail herein.

Thus, exercise device 200 differs from the exercise devices 100, 100A, 100B and 100C in that exercise device 200 includes an electronic angle indicator 2300.

The exercise device 200 again includes handle 202 that is identical to handle 102, except as described herein, and which has a proximal portion 202a and a distal portion 202b. In a similar manner as shaft 110 that defines longitudinal axis X-X that extends from proximal end 110a to distal end 110b, shaft 210 also defines a longitudinal axis (not shown) that extends from a proximal end (not shown) to a distal end (not shown).

In a similar manner, head portion 220 has a predetermined weight. The head portion 220 or the handle 202 are mounted for relative movement on the shaft 210 between a first position and a second position as described above. Therefore, the predetermined weights W1, W2, W3 and distances D1, D2, D3, D4 are applied in the same manner to produce the effective torques T1, T2, T3, T4 for the Settings 1, 2, 3, 4 as shown in FIG. 6.

In a similar manner as described above with respect to electronic device 100 in FIGS. 20 and 21, the electronic angle indicator 2300 includes a plurality of concentric beads 234 on the angle indicator 2300 that extend in an arc of 180° on the periphery of the distal semi-circular portion of the angle indicator to include beads 234a . . . 234n wherein line HL drawn across the angle indicator 2300 from bead 234a to bead 234n is perpendicular to the central line CL and bead 234g is aligned with the central line CL. Thus, the arcs defined by beads 234a to 234g and beads 234g to 234n are each 90° and the beads 234a and 234n each at the most extreme lateral position from central line CL. In a similar manner to stationary bead 134', stationary bead 234' is disposed at the proximal most position of the circular electronic angle indicator 2300 and in alignment with the central line CL.

As also described above for FIGS. 20-21 and mechanical angle indicator 130 regarding if an arrow is drawn from the center C of the angle indicator 130 to the bubble B, the arrow will always point upwards in a direction parallel to the vertical line in space VL and that the arc of beads 134a . . . 134n always moves as the exercise device 100 is moved.

In a similar manner to the concept of the arrow, electronic angle indicator 2300 includes a series of dots 236a . . . 236n with 6 dots shown as an example. The dots are analogous to the arrow drawn between the center C of the bubble angle indicator 132 and the bubble B. Therefore, the dots point to the position on the arc of beads 234a . . . 234n that represents the angle Φ1 between the arrow represented by the dots 236a . . . 236n, and which are parallel to the vertical line in space VL, and the central line CL in the central plane CP. In the example shown in FIGS. 22 and 23, the angle Φ1 is approximately 45° and is digitally displayed on the angle indicator 2300.

Figure 24A:
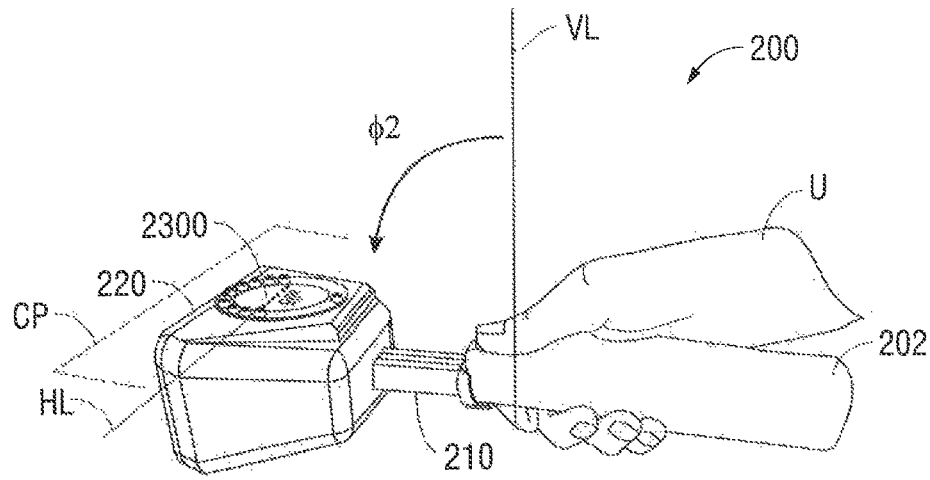
FIG. 24A illustrates a partial view of the exercise device of FIGS. 22 and 23 with the electronic angle indicator in a mode of operation in the same position as shown in FIG. 12 for wrist deviator exercises.
Figure 24B:
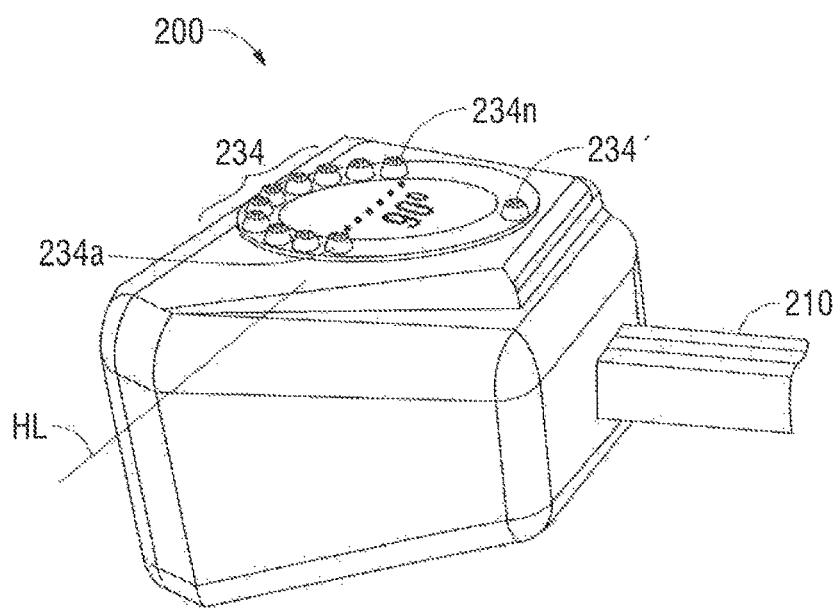
FIG. 24B is a detailed view of the electronic angle indicator of the exercise device of FIG. 24A.

In the same manner as described above with respect to FIGS. 7 and 8, FIGS. 24A and 24B illustrate a partial view of the exercise device 200 with the electronic angle indicator 2300 in a mode of operation in the same position as shown in FIG. 12 for wrist deviator exercises using the exercise device 100 with the mechanical bubble angle indicator 132. More particularly, in FIG. 24A, the central plane CP of the exercise device 200 is coincident with reference horizontal plane HP that is perpendicular to the reference vertical line VL in space.

In a similar manner, the reference angle indicator line AI' is drawn through the center C of the electronic angle indicator 2300 and which is perpendicular to the central plane CP and, for the position shown, the angle indicator line AI' is perpendicular to the reference horizontal plane HP. Therefore, the angle θ1 in FIG. 24 is also zero since the angle indicator line AI' and the reference vertical line VL are parallel to one another.

A reference horizontal line HL is drawn through beads 234a and 234n so that the horizontal line HL is a reference line that is perpendicular to the central line CL Accordingly, the angle θ2 in FIG. 24 is 90°.

In embodiments, the beads in the arc of beads 234 may be electrical or electronic lights that illuminate to coincide with the position of the arrow and therefore the angle measurement (for FIGS. 22 and 23).

Figure 25:
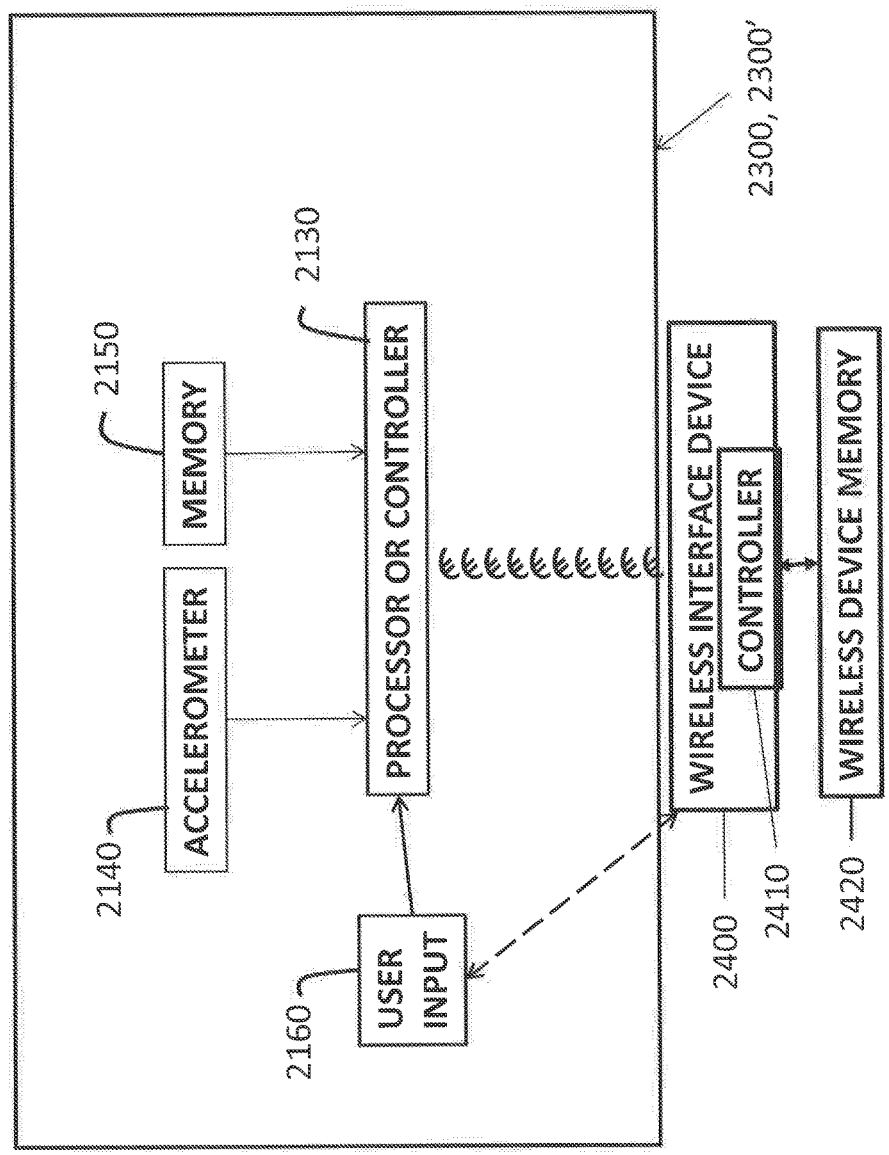
FIG. 25 is a schematic diagram of the electronic angle indicator including a processor or controller and an accelerometer that is disposed within the exercise device of FIGS. 22-24B.

Referring also to FIGS. 22 and 25, the electronic angle indicator 2300 includes a processor or controller 2130 that is disposed within the exercise device 200, e.g., either within the head portion 220 or within handle 202' as electronic angle indicator 2300' in shaft 202' which is an extended version of shaft 202.

The electronic angle indicators 2300 and 2300' are configured and function in a similar manner to other devices known in the art such as the input device described in, for example, U.S. Pat. No. 7,337,549 "INPUT DEVICE FOR USING GEOMAGNETIC SENSOR AND A METHOD THEREOF FOR GENERATING INPUT SIGNAL", by Cho et al., the entire contents of which are incorporated by reference herein, and as further modified by more recent developments in accelerometers which now enable measurement of both static acceleration to determine the angle at which the exercise device 200 is tilted with respect to the earth's axis of rotation and dynamic acceleration that determines the relative motion of the device with respect to the angle at which the exercise device 200 is tilted with respect to the earth's axis of rotation. In the state of the art accelerometers, the function of the geomagnetic sensor may now be performed by a 3-dimensional (3D) accelerometer, such as, for example, a Buffered 3D Accelerometer, Model No. DE-ACCM3D, manufactured by Dimension Engineering, Hudson, Ohio, USA.

In embodiments, turning to FIG. 25, electronic angle indicators 2300 and 2300' include a processor or controller 2130, an accelerometer 2140, a memory 2150 and user input 2160.

The processor or controller 2130 compares a current azimuth to a previous azimuth stored in the memory 2150, thereby determining a rotation degree.

The accelerometer 2140 includes and X-axis accelerometer, a Y-axis accelerometer and a Z-axis accelerometer perpendicularly mounted to each other to calculate the various angles using the voltage measured by the accelerometer 2140 of each axis.

To select exercise settings as described below with respect to FIGS. 26 and 27, the user input 2160 may include direction keys and numeric keys or may include a touch screen or voice activated input. The user input 2160 may include a wireless interface device 2400 having a controller 2410 that communicates wirelessly with the processor or controller 2130. The wireless controller 2410 is in electrical communication with wireless device memory 2420 that may reside in the wireless interface device 2400 or may be memory stored in an external server (e.g., "the cloud").

Besides the threshold, the memory 2150 stores information on the previous azimuth, a normalizing factor, maximum and minimum values of the X-axis output, Y-axis and Z-axis output (the vertical line VL in space), and the sensitivity.

Thus, the processor or controller 2130 or 2410 is configured to execute instructions in real time to cause electronically driven arrow 236 to point to variable positions that indicate the angle between the central line in the central plane and a vertical line in space at which a user has positioned the exercise device.

The processor or controller 2130 or 2410 can be a processor, microcontroller, a system on chip (SOC), field programmable gate array (FPGA), etc. Collectively the one or more components, which can include a processor, microcontroller, SOC, and/or FPGA, for performing the various functions and operations described herein are part of a controller, as recited, for example, in the claims. The controller may be provided as a single integrated circuit (IC) chip which may be mounted on a single printed circuit board (PCB). Alternatively, the various circuit components of the controller, including, for example, the processor, microcontroller, etc. are provided as one or more integrated circuit chips. That is, the various circuit components are located on one or more integrated circuit chips.

The settings, countdowns, measurements, signals and displays may be entirely or partially established in the processor 2130 of the electronic angle indicators 2300 or 2300' on the electronic exercise device 200 itself or else established entirely or partially in the processor 2410 of the wireless interface device 2400 and the both processors 2130 and 2410 are in electrical communication with one another to ascertain the settings, countdowns, measurements, signals and displays established in the other processor.

Thus, some of the foregoing features may be available as a stand-alone on the electronic exercise device 200 itself and some must be used with the wireless interface device 2400. For example, the audio signal may be generated from the electronic exercise device 200 itself and the countdown from the wireless interface device 2400, etc.

Wrist Deviator is a hammering motion. So, for a patient, it is desirable to get the full range of motion where the exercise device is initially aligned with the vertical line in space VL and then be moved to align with the horizontal plane HP in a hammering motion in an arc of 90°. Persons with injuries may be unable to perform such a range of motion and are only able to move the exercise device to a limited degree, e.g., only 45°.

Supination and Pronation involve the rotation of the exercise device in a clockwise and counter-clockwise motion from −90° to +90°. Again, persons with injuries may be unable to perform such a range of motion and may only able to move the exercise device to a limited degree, e.g., only 45°.

A therapist may set the MAX angle wishes the patient to go for any exercise. For pronation/supination, the therapist may set the device to produce a signal when it rotates −70 degrees and +60 degrees. The settings do not need to be symmetrical. Some patients are recovering from an injury and the therapist may not desire exercising for the full +90/−90 degrees. Once the patient has gone that far, the unit may produce a beep (either on the wireless interface device or on the exercise device itself). Therefore, the patient would know he or she has accomplished the MAX torque and/or angle level he or she should go. The patient may then exercise in the other direction until he or she hears a beep. The exercise cycle may then be repeated.

In VISUAL signal mode, the patient can see the angle that should be accomplished, at any one time, by looking at the screen on the exercise device or on the wireless interface device. So, in a similar manner as the above example, the patient may only be supposed to reach −70 degrees and is only able to reach 65 degrees as seen by the line on the screen (and text).

As for COUNTDOWN, the therapist may ask the patient to perform the exercise 10 times. After each clockwise and counter-clockwise rotation, the wireless device can say, "10", then "9" after the next complete set, then "8", etc. . . . until "Completed" is heard.

Again, the exercise routines and settings possible to be established on the exercise device and on the wireless interface device are flexible and able to be customized for the individual patient's requirements.

Figure 26:
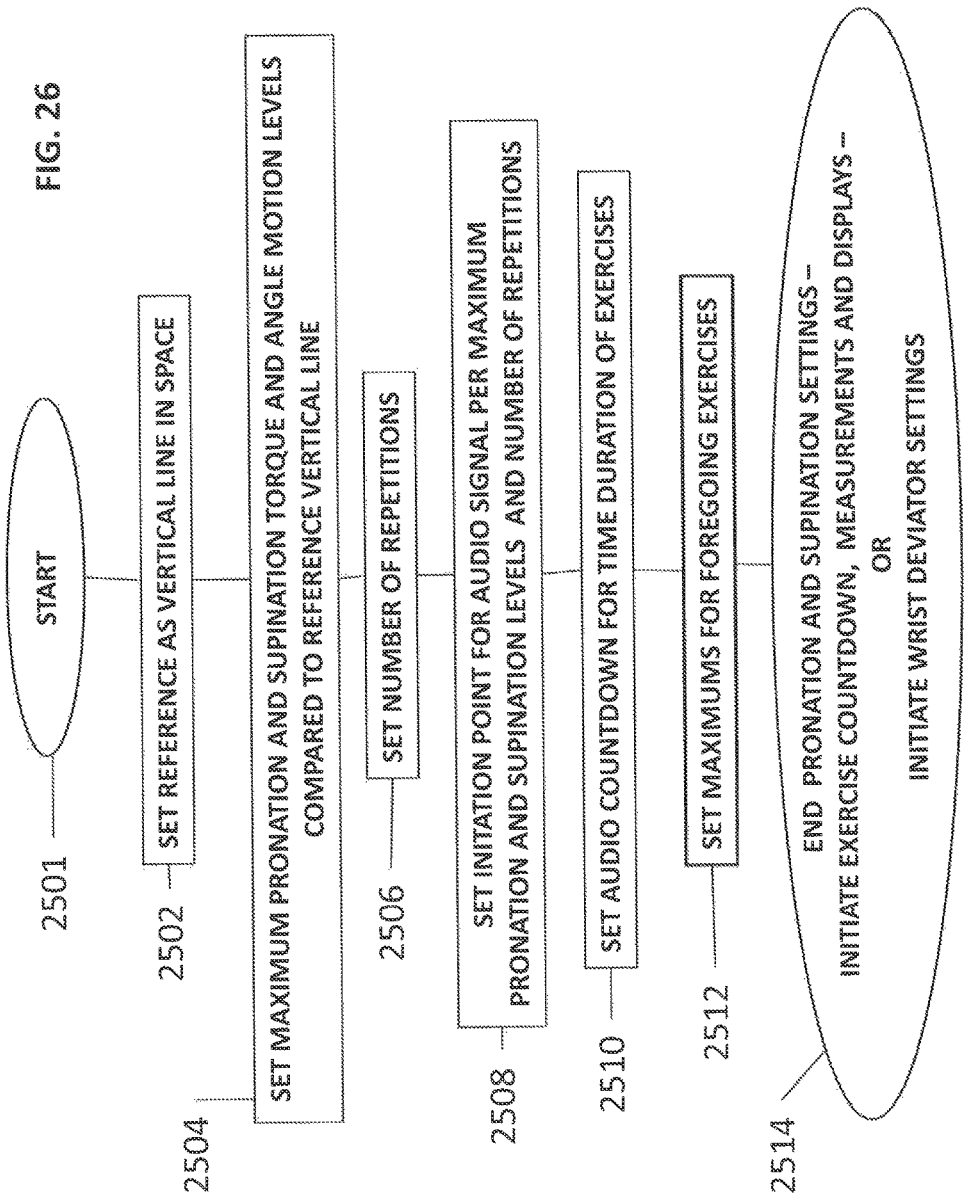
FIG. 26 illustrates a method of therapeutic exercise via a predetermined weighted exercise device, such as the exercise devices of FIGS. 1-25 that includes setting pronation and supination exercise levels for the exercise devices.

FIG. 26 illustrates a method 2500 of therapeutic exercise via a predetermined weighted exercise device, such as the exercise devices 100, 100A, 100B, 100C or 200 that includes, after a start 2501, a step of 2502 of setting a reference as a vertical line in space, e.g., reference vertical line VL in space as described with respect to FIGS. 7-12, etc. The method includes step 2504 of setting maximum and minimum pronation and supination torque levels, e.g., T1=W1×D1, T2=W1×D2, T3=W1×D3, T4=W1×D4, etc. and angle motion levels, e.g. angles $\Phi1$, $\Phi1'$, etc. and $\alpha1$, $\alpha1'$, $\alpha1''$, etc. compared to the reference vertical line VL that is imagined in space or set in a processor or control part, e.g., processor or control part 2130 of electronic angle indicator 2300 or 2300', or processor or control part 2410 of separate wireless interface device 2400, etc.

In embodiments, the method may further include step 2506 of setting, when applicable in the processor or control part 2130 or 2410, the number of repetitions desired for the pronation-supination exercises.

In embodiments, the method may further include step 2508 of setting, when applicable in the processor or control part, an initiation point or initiation points for audio signals according to maximum desired pronation and supination levels set in step 2504 and maximum number of repetitions set in step 2506.

In embodiments, the method may further include step 2510 of setting, when applicable in the processor or control part, an audio countdown for time duration of the foregoing pronation-supination exercises.

In embodiments, the method may further include step 2512 of setting, when applicable in the processor or control part, maximum values for some or all of the foregoing pronation-supination exercises.

In embodiments, the method may further include step 2514 of either ending setting of the pronation and supination levels of the foregoing steps 2501 to 2512 and initiating exercises including countdowns, measurements and displays via the mechanical exercise devices 100, 100A, 100B, 100C or electronic exercise device 200 or initiating wrist deviator settings for those devices.

Figure 27:
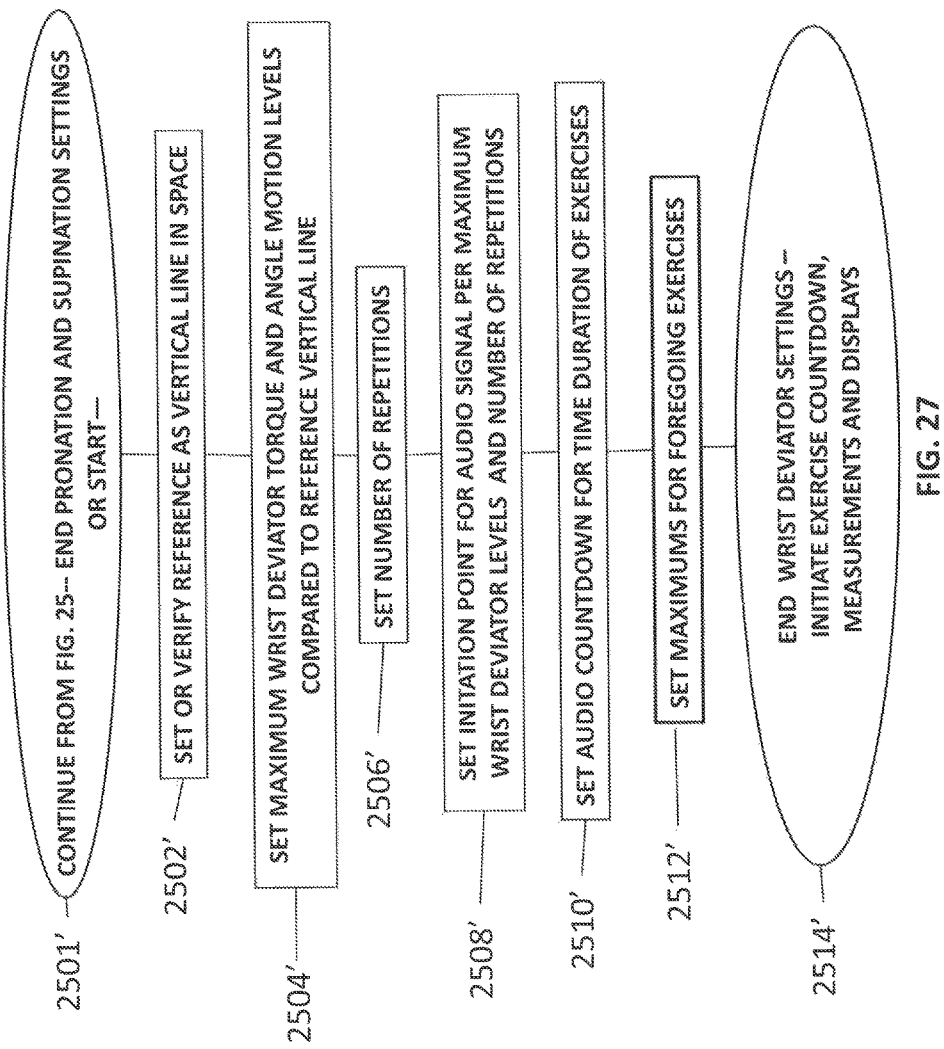
FIG. 27 illustrates a method of therapeutic exercise via a predetermined weighted exercise device, such as the exercise devices of FIGS. 1-25 that includes setting wrist deviator exercise levels for the exercise devices.

FIG. 27 illustrates method 2500' of therapeutic exercise via a predetermined weighted exercise device, such as the exercise devices 100, 100A, 100B, 100C or 200 that either is a continuation 2500' of the method 2500 of step 2514 wherein in step 2500', the pronation and supination settings have been completed or wrist deviator settings of the exercise devices 100, 100A, 100B, 100C or 200 are initiated independently. The method 2500' may include a step 2502' of setting a reference as a vertical line in space, e.g., reference vertical line VL in space as described with respect to FIGS. 7-12, etc., or verifying the reference setup of step 2502 in FIG. 26.

The method 2500' includes step 2504' of setting maximum and minimum wrist deviator torque levels, e.g., T1=W1×D1, T2=W1×D2, T3=W1×D3, T4=W1×D4, etc. and angle motion levels, e.g. angles θ1, θ2 etc. compared to the reference vertical line VL that is imagined in space or set in a processor or control part, e.g., processor or control part 2130 of electronic angle indicator 2300 or 2300' or 2300 or 2300', or processor or control part 2410 of wireless interface device 2400, etc.

In embodiments, the method 2500' may further include step 2506' of setting, when applicable in the processor or control part 2130 or 2410, the number of repetitions desired for the wrist deviator exercises.

In embodiments, the method 2500' may further include step 2508' of setting an initiation point or initiation points for audio signals according to maximum desired wrist deviator levels set in step 2504' and maximum number of repetitions set in step 2506'.

In embodiments, the method 2500' may further include step 2510' of setting an audio countdown for time duration of the foregoing wrist deviator exercises.

In embodiments, the method 2500' may further include step 2512' of setting maximum values for some or all of the foregoing wrist deviator exercises.

In embodiments, the method 2500' may further include step 2514' of ending the setting of the wrist deviator levels of the foregoing steps 2501' to 2512' and initiating the wrist deviator exercises including countdowns, measurements and displays via the mechanical exercise devices 100, 100A, 100B, 100C or electronic exercise device 200.

Those skilled in the art will recognize that the angle measurements for the various exercise devices described above may be imagined by assuming that the vertical line in space VL is the Z-axis of an X-Y-Z axis coordinate system wherein the pronation-supination exercises involve yaw measurements or deviations in the Y-Z plane from the Z-axis while the wrist deviator exercises involve pitch measurements or deviations in the X-Z plane from the Z-axis.

It should be noted also that the steps relating to setting levels and maximum settings in methods 2500 and 2500' may generally be performed in any order convenient for the user and not necessarily in the sequences illustrated in FIGS. 26 and 27.

Although the present disclosure has been described in considerable detail with reference to certain embodiments, other embodiments and versions are possible and contemplated. Therefore, the spirit and scope of the appended claims should not be limited to the description of the embodiments contained herein.

What is claimed is:

1. A pronation supination wrist deviator exercise device comprising:
   a handle having a proximal portion and a distal portion;
   a shaft having a proximal end and a distal end, the shaft defining a longitudinal axis extending from the proximal end of the shaft to the distal end of the shaft;
   a head portion having a predetermined weight, the head portion or the handle mounted for relative movement on the shaft between a first position and a second position;
   a central plane defined through the handle and the head portion and a central line in the central plane extending through the handle and the head portion, wherein the exercise device is positionable by a user at an angle between the central line in the central plane and a vertical line in space; and
   an angle indicator that indicates the angle between the central line in the central plane and the vertical line in space, the angle indicator being a bubble indicator, the bubble indicator comprising a plurality of stationary beads circumferentially disposed in a curved path and a bubble supported in the bubble indicator, the bubble positioned to move to variable positions indicating the angle between the central line in the central plane and the vertical line in space.

2. The exercise device according to claim 1, wherein the head portion and the handle on the shaft define a first distance between the head portion and the distal portion of the handle, wherein the predetermined weight of the head portion represents a first weight, the first weight multiplied by the first distance representing a first effective torque of the pronation supination wrist deviator exercise device, and wherein the distance between the head portion and the distal portion of the handle is changed to a second distance, the first weight multiplied by the second distance representing a second effective torque of the pronation supination wrist deviator exercise device.

3. The exercise device according to claim 1, wherein the head portion and the handle on the shaft define a first distance between the head portion and the distal portion of the handle, wherein the predetermined weight of the head portion is changed to a second weight, the second weight multiplied by the first distance representing a second effective torque of the pronation supination wrist deviator exercise device.

4. The exercise device according to claim 2, wherein when head portion and the handle on the shaft define a second distance between the head portion and the distal portion of the handle, the predetermined weight of the head portion is changed to a second weight, the second weight multiplied by the second distance representing another effective torque of the pronation supination wrist deviator exercise device.

5. The exercise device according to claim 3, wherein the head portion and the handle on the shaft define a second distance between the head portion and the distal portion of the handle, wherein, the second weight multiplied by the second distance representing at least another effective torque of the pronation supination wrist deviator exercise device.

6. The exercise device according to claim 1, wherein the handle further comprises a manually operable release collar that secures the handle to the shaft, the manually operable release collar enabling the user to secure the handle to and release the handle from various positions on the shaft to adjust distance between a proximal portion of the handle and the head portion.

7. The exercise device according to claim 1, wherein the angle indicator indicates the angle at which the user positioned the exercise device when the central plane is parallel to the vertical line in space.

8. The exercise device according to claim 1, wherein the angle indicator indicates the angle at which the user positioned the exercise device when the central plane is perpendicular to the vertical line in space.

9. The exercise device according to claim 1, wherein the angle indicator indicates the angle at which the positioned the exercise device when the central plane is skewed to the vertical line in space.

10. A pronation supination wrist deviator exercise device comprising:
a handle having a proximal portion and a distal portion;
a shaft having a proximal end and a distal end, the shaft defining a longitudinal axis extending from the proximal end of the shaft to the distal end of the shaft;
a head portion having a predetermined weight, the head portion or the handle mounted for relative movement on the shaft between a first position and a second position;
a central plane defined through the handle and the head portion and a central line in the central plane extending through the handle and the head portion, wherein the exercise device is positionable by a user at an angle between the central plane and a vertical line in space; and
an angle indicator that indicates the angle between the central plane and the vertical line in space, the angle indicator being a bubble indicator, the bubble indicator supporting a bubble therein and comprising a transparent compartment having an outer surface and confining a volume of fluid extending from a portion of the central plane and a plurality of concentric circles disposed on the outer surface, wherein the bubble is positioned to move to variable positions indicating the angle between the central plane and the vertical line in space.

11. A pronation supination wrist deviator exercise device comprising:
a handle;
a shaft coupled to the handle;
a head portion coupled to the shaft and positioned for relative movement with respect to the handle between a first position and a second position; and
a bubble indicator supporting a bubble and including a plurality of stationary beads disposed in a curved path, the bubble positioned to move relative to the plurality of stationary beads to indicate angular movement of the exercise device.

12. The exercise device according to claim 11, wherein relative movement between the head portion and the handle changes effective torque output by the pronation supination wrist deviator exercise device.

13. The exercise device according to claim 12, wherein distance between the head portion and the handle increases in response to movement between the first and second positions, effective torque output by the pronation supination wrist deviator exercise device increases.

14. The exercise device according to claim 13, wherein distance between the head portion and the handle decreases in response to movement between the first and second positions, effective torque output by the pronation supination wrist deviator exercise device decreases.

15. The exercise device according to claim 11, wherein relative movement between the head portion and the handle is in an axial direction relative to a longitudinal axis defined by the shaft.

16. The exercise device according to claim 11, wherein the handle further comprises a release collar that selectively secures the handle in various positions relative to the shaft, the head portion, or combinations thereof.

* * * * *